United States Patent
Chang et al.

(10) Patent No.: US 9,534,045 B2
(45) Date of Patent: *Jan. 3, 2017

(54) PHOENIXIN PEPTIDES

(71) Applicant: Phoenix Pharmaceuticals, Inc., Burlingame, CA (US)

(72) Inventors: Jaw-Kang Chang, San Carlos, CA (US); Rong-Ming Lyu, Foster City, CA (US)

(73) Assignee: Phoenix Pharmaceuticals, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/697,530

(22) Filed: Apr. 27, 2015

(65) Prior Publication Data

US 2015/0322141 A1 Nov. 12, 2015

Related U.S. Application Data

(63) Continuation of application No. 14/119,866, filed as application No. PCT/US2012/039743 on May 25, 2012, now Pat. No. 9,018,350.

(60) Provisional application No. 61/519,746, filed on May 28, 2011, provisional application No. 61/519,747, filed on May 26, 2011.

(51) Int. Cl.
| | |
|---|---|
| *C07K 7/06* | (2006.01) |
| *C07K 7/08* | (2006.01) |
| *A61K 38/00* | (2006.01) |
| *C07K 16/18* | (2006.01) |
| *C07K 14/47* | (2006.01) |
| *C07K 14/575* | (2006.01) |
| *C07K 14/705* | (2006.01) |
| *A61K 39/00* | (2006.01) |

(52) U.S. Cl.
CPC ............... *C07K 16/18* (2013.01); *C07K 7/08* (2013.01); *C07K 14/4702* (2013.01); *C07K 14/575* (2013.01); *C07K 14/705* (2013.01); *A61K 38/00* (2013.01); *A61K 2039/505* (2013.01)

(58) Field of Classification Search
CPC ..... C07K 16/18; C07K 14/575; C07K 14/705; C07K 7/08; C07K 14/4702; A61K 2039/505; A61K 38/00
See application file for complete search history.

(56) References Cited

U.S. PATENT DOCUMENTS

| | | |
|---|---|---|
| 5,441,936 A | 8/1995 | Houghten et al. |
| 8,313,914 B2 | 11/2012 | Finlayson et al. |
| 2005/0221359 A1 | 10/2005 | Hsueh et al. |
| 2014/0163202 A1 | 6/2014 | Chang et al. |

FOREIGN PATENT DOCUMENTS

| | | | | |
|---|---|---|---|---|
| WO | WO 99/10363 A1 * | 3/1999 | ............. | C07H 21/00 |
| WO | WO 2006/018315 | 2/2006 | | |

OTHER PUBLICATIONS

Lyu et al. Phoenixin: A novel peptide in rodent sensory ganglia. Neuroscience, Oct. 2013, vol. 250, pp. 622-631.
Yosten et al. A Novel Reproductive Peptide, Phoenixin. J of Neuroendocrinology, Jan. 2013, vol. 25, No. 2, pp. 206-215.
Corresponding European Patent Application No. 12789015.0; Office Action mailed Feb. 19, 2015, 16 pages total.
Corresponding Chinese Patent Application No. 201280036356.X; Office Action mailed Apr. 1, 2015, 18 pages total.
Cowan et al. A Candidate Pruritogen in the Mouse. Neuroscience, Dec. 2015, vol. 310, pp. 541-548.
U.S. Appl. No. 61/519,747, filed May 26, 2011.
U.S. Appl. No. 61/519,746, filed May 28, 2011.
PCT Interantional Patent Application No. PCT/US2012/039743, filed May 25, 2012.
Lyu et al. Isolation, Identification, and Distribution of Phoenixin. Proceedings of the 22nd American Peptide Symposium, Jun. 2011, San Diego, CA, pp. 214-215.
Wei et al. d-amino acid-substituted analogs of corticotropin-releasing hormone (CRH) and urocortin with selective agonist activity at CRH1 and CRH2β receptors. Peptides, Jul. 1998, vol. 19, Issue 7, pp. 1183-1190.
Corresponding EP Patent Application No. 12789015.0; Office Action mailed Nov. 26, 2014, 7 total pages.

* cited by examiner

*Primary Examiner* — Julie Ha
*Assistant Examiner* — Li Ni Komatsu
(74) *Attorney, Agent, or Firm* — Craig R. Miles; CR Miles P.C.

(57) ABSTRACT

Human phoenixin peptides, analogs and mimetics useful in production of anti-phoenixin antibodies, diagnostic screening and assays, and in modulating cellular concentration of cAMP, and treatment of disorders related to cAMP or $Ca^{2+}$ concentration in cells, modulating hypertension and cardiovascular function, modulating gonadotrophs and gastric emptying.

7 Claims, 24 Drawing Sheets

Met-Val-Lys-Glu-Val-Trp-Arg-Val-Leu-Arg-Glu-Glu-Pro-Gly-Arg-
1                        5                        10                       15
Arg-Lys-Glu-Ser-Arg-Gln-Asn-Arg-Ala-Arg-Gly-Asn-Arg-Val-Gln-
16                       20                       25                       30
Gln-Asn-Ser-Ser-Asn-Leu-Asn-Pro-Thr-Pro-Ala-Pro-Gly-Pro-His-
31                       35                       40                       45
Ser-Thr-Glu-Ser-Arg-Gly-Arg-Arg-Gly-Ala-Gly-Ser-Glu-Ala-Pro-
46                       50                       55                       60
Pro-Arg-Pro-Gly-Ser-Glu-Ser-Leu-Ser-Thr-Ser-Ser-Glu-Arg-Gly-
61                       65                       70                       75
His-Gly-Pro-Ala-Val-Gly-Asn-Leu-Val-Ser-Glu-Ser-Ala-Gly-Arg-
76                       80                       85                       90
Ser-Ala-Gly-Gln-Gly-Ser-Pro-Gly-Pro-Asp-Ala-Met-Ser-Arg-Asn-
91                       95                       100                      105
Leu-Arg-Thr-Ala-Leu-Ile-Phe-Gly-Gly-Phe-Ile-Ser-Leu-Ile-Gly-
106                      110                      115                      120
Ala-Ala-Phe-Tyr-Pro-Ile-Tyr-Phe-Arg-Pro-Leu-Met-Arg-Leu-Glu-
121                      125                      130                      135
Glu-Tyr-Lys-Lys-Glu-Gln-Ala-Ile-Asn-Arg-Ala-Gly-Ile-Val-Gln-
136                      140                      145                      150
Glu-Asp-Val-Gln-Pro-Pro-Gly-Leu-Lys-Val-Trp-Ser-Asp-Pro-Phe-
151                      155                      160                      165
Gly-Arg-Lys
166     168
(SEQ. ID NO: 1)

FIG. 1

Ala-Gly-Ile-Val-Gln-Glu-Asp-Val-Gln-Pro-Pro-Gly-Leu-Lys-Val-Trp-Ser-Asp-Pro-Phe
1            5                    10                  15                  20
(SEQ. ID NO: 2)

FIG. 2

Asp-Val-Gln-Pro-Pro-Gly-Leu-Lys-Val-Trp-Ser-Asp-Pro-Phe-Gly
(SEQ. ID NO: 3)

FIG. 3

Asp-Val-Gln-Pro-Pro-Gly-Leu-Lys-Val-Trp-Ser-Asp-Pro-Phe
(SEQ. ID NO: 4)

FIG. 4

Gln-Pro-Pro-Gly-Leu-Lys-Val-Trp-Ser-Asp-Pro-Phe-Gly
(SEQ. ID NO: 5)

FIG. 5

Val-Gln-Pro-Pro-Gly-Leu-Lys-Val-Trp-Ser-Asp-Pro-Phe
(SEQ. ID NO: 6)

FIG. 6

Ala-Gly-Ile-Val-Gln-Glu-Asp-Val-Gln-Pro-Pro-Gly-Leu-Lys-Val-Trp-Ser-Asp-Pro-Phe-NH2
(SEQ. ID NO: 7)

FIG. 7

Val-Gln-Pro-Pro-Gly-Leu-Lys-Val-Trp-Ser-Asp-Pro-Phe-NH2
(SEQ. ID NO: 8)

FIG. 8

Asp-Val-Gln-Pro-Pro-Gly-Leu-Lys-Val-Trp-Ser-Asp-Pro-Phe-NH2
(SEQ. ID NO: 9)

FIG. 9 pGlu-Glu-Asp-Val-Gln-Pro-Pro-Gly-Leu-Lys-Val-Trp-Ser-Asp-Pro-Phe-NH2
(SEQ. ID NO: 10)

FIG. 10

Gln-Pro-Pro-Gly-Leu-Lys-Val-Trp-Ser-Asp-Pro-Phe-NH2
(SEQ. ID NO: 11)

FIG. 11 pGlu-Pro-Pro-Gly-Leu-Lys-Val-Trp-Ser-Asp-Pro-Phe-NH2
(SEQ. ID NO: 12)

FIG. 12

Ala-Gly-Ile-Val-Gln-Glu-Asp-Val-Gln-Pro-Pro-Gly-Leu-Lys-Val-Trp-Ser-Asp-Pro-Phe-NHCH3
(SEQ. ID NO: 13)

FIG. 13

Val-Gln-Pro-Pro-Gly-Leu-Lys-Val-Trp-Ser-Asp-Pro-Phe-NHCH3
(SEQ. ID NO: 14)

FIG. 14

Asp-Val-Gln-Pro-Pro-Gly-Leu-Lys-Val-Trp-Ser-Asp-Pro-Phe-NHCH3
(SEQ. ID NO: 15)

FIG. 15 pGlu-Glu-Asp-Val-Gln-Pro-Pro-Gly-Leu-Lys-Val-Trp-Ser-Asp-Pro-Phe-NHCH3
(SEQ. ID NO: 16)

FIG. 16

Gln-Pro-Gly-Leu-Lys-Val-Trp-Ser-Asp-Pro-Phe-NHCH3
(SEQ. ID NO: 17)

FIG. 17 pGlu-Pro-Pro-Gly-Leu-Lys-Val-Trp-Ser-Asp-Pro-Phe-NHCH3
(SEQ. ID NO: 18)

FIG. 18

Ala-Gly-Ile-Val-Gln-Glu-Asp-Val-Gln-Pro-Pro-Gly-Leu-Lys-Val-Trp-Ser-Asp-Pro-Phe-NHCH2CH3
(SEQ. ID NO: 19)

FIG. 19

Val-Gln-Pro-Pro-Gly-Leu-Lys-Val-Trp-Ser-Asp-Pro-Phe-NH CH2CH3
(SEQ. ID NO: 20)

FIG. 20

Asp-Val-Gln-Pro-Pro-Gly-Leu-Lys-Val-Trp-Ser-Asp-Pro-Phe-NH CH2CH3
(SEQ. ID NO: 21)

FIG. 21 pGlu-Glu-Asp-Val-Gln-Pro-Pro-Gly-Leu-Lys-Val-Trp-Ser-Asp-Pro-Phe-NH CH2CH3
(SEQ. ID NO: 22)

FIG. 22

Gln-Pro-Pro-Gly-Leu-Lys-Val-Trp-Ser-Asp-Pro-Phe-NH CH2CH3
(SEQ. ID NO: 23)

FIG. 23 pGlu-Pro-Pro-Gly-Leu-Lys-Val-Trp-Ser-Asp-Pro-Phe-NH CH2CH3
(SEQ. ID NO: 24)

FIG. 24

Asp-dVal-Gln-Pro-Pro-Gly-Leu-Lys-Val-Trp-Ser-Asp-Pro-Phe-NH2
(SEQ. ID NO: 25)

FIG. 25

Asp-Val-Gln-dPro-Pro-Gly-Leu-Lys-Val-Trp-Ser-Asp-Pro-Phe-NH2
(SEQ. ID NO: 26)

FIG. 26

Asp-Val-Gln-Pro-dPro-Gly-Leu-Lys-Val-Trp-Ser-Asp-Pro-Phe-NH2
(SEQ. ID NO: 27)

FIG. 27

Asp-Val-Gln-Pro-Pro-dAla-Leu-Lys-Val-Trp-Ser-Asp-Pro-Phe-NH2
(SEQ. ID NO: 28)

FIG. 28

Asp-Val-Gln-Pro-Pro-Gly-dLeu-Lys-Val-Trp-Ser-Asp-Pro-Phe-NH2
(SEQ. ID NO: 29)

FIG. 29

Asp-Val-Gln-Pro-Pro-Gly-Leu-Lys-dVal-Trp-Ser-Asp-Pro-Phe-NH2
(SEQ. ID NO: 30)

FIG. 30

Asp-Val-Gln-Pro-Pro-Gly-Leu-Lys-Val-dTrp-Ser-Asp-Pro-Phe-NH2
(SEQ. ID NO: 31)

FIG. 31

Asp-Val-Gln-Pro-Pro-Gly-Leu-Lys-Val-Trp-Ser-Asp-dPro-Phe-NH2
(SEQ. ID NO: 32)

FIG. 32

Asp-Val-Gln-Pro-Pro-Gly-Leu-Lys-Val-Trp-Ser-Asp-Pro-dPhe-NH2
(SEQ. ID NO: 33)

FIG. 33

Asp-Val-Gln-Pro-Pro-Gly-Leu-Lys-Val-Trp-Ser-Asp-Pro-dTic-NH2
(SEQ. ID NO: 34)

FIG. 34 dAla-Gly-Ile-Val-Gln-Glu-Asp-Val-Gln-Pro-Pro-Gly-Leu-Lys-Val-Trp-Ser-Asp-Pro-Phe-NH2
(SEQ. ID NO: 35)

FIG. 35

Ala-dAla-Ile-Val-Gln-Glu-Asp-Val-Gln-Pro-Pro-Gly-Leu-Lys-Val-Trp-Ser-Asp-Pro-Phe-NH2
(SEQ. ID NO: 36)

FIG. 36

Ala-Gly-Ile-dVal-Gln-Glu-Asp-Val-Gln-Pro-Pro-Gly-Leu-Lys-Val-Trp-Ser-Asp-Pro-Phe-NH2
(SEQ. ID NO: 37)

FIG. 37

Ala-Gly-Ile-Val-Gln-Glu-Asp-dVal-Gln-Pro-Pro-Gly-Leu-Lys-Val-Trp-Ser-Asp-Pro-Phe-NH2
(SEQ. ID NO: 38)

FIG. 38

Ala-Gly-Ile-Val-Gln-Glu-Asp-Val-Gln-Pro-Pro-Gly-Leu-Lys-Val-Trp-dSer-Asp-Pro-Phe-NH2
(SEQ. ID NO: 39)

FIG. 39

Ala-Gly-Ile-Val-Gln-Glu-Asp-Val-Gln-Pro-Pro-Gly-Leu-Lys-Val-Trp-Ser-Asp-dPro-Phe-NH2
(SEQ. ID NO: 40)

FIG. 40

Ala-Gly-Ile-Val-Gln-Glu-Asp-Val-Gln-Pro-Pro-Gly-Leu-Lys-Val-Trp-Ser-Asp-Pro-dPhe-NH2

(SEQ. ID NO: 41)

FIG. 41

Ac-Ala-Gly-Ile-Val-Gln-Glu-Asp-Val-Gln-Pro-Pro-Gly-Leu-Lys-Val-Trp-Ser-Asp-Pro-Phe-NH2

(SEQ. ID NO: 42)

FIG. 42

Ac-Val-Gln-Pro-Pro-Gly-Leu-Lys-Val-Trp-Ser-Asp-Pro-Phe-NH2

(SEQ. ID NO: 43)

FIG. 43

Ac-Asp-Val-Gln-Pro-Pro-Gly-Leu-Lys-Val-Trp-Ser-Asp-Pro-Phe-NH2

(SEQ. ID NO: 44)

FIG. 44

Fom-Ala-Gly-Ile-Val-Gln-Glu-Asp-Val-Gln-Pro-Pro-Gly-Leu-Lys-Val-Trp-Ser-Asp-Pro-Phe-NH2

(SEQ. ID NO: 45)

FIG. 45

Fom-Glu-Asp-Val-Gln-Pro-Pro-Gly-Leu-Lys-Val-Trp-Ser-Asp-Pro-Phe-NH2
(SEQ. ID NO: 46)

FIG. 46

Fom-Asp-Val-Gln-Pro-Pro-Gly-Leu-Lys-Val-Trp-Ser-Asp-Pro-Phe-NH2
(SEQ. ID NO: 47)

FIG. 47

Ala-Gly-Ile-Val-Gln-Glu-Asp-Val-Gln-Pro-Pro-Gly-Leu-Lys-Val-Trp-Ser-Asp-Pro-Nap
(SEQ. ID NO: 48)

FIG. 48

Asp-Val-Gln-Pro-Pro-Gly-Leu-Lys-Val-Trp-Ser-Asp-Pro-Nap
(SEQ. ID NO: 49)

FIG. 49

Val-Gln-Pro-Pro-Gly-Leu-Lys-Val-Trp-Ser-Asp-Pro-Nap
(SEQ. ID NO: 50)

FIG. 50 pGlu-Glu-Asp-Val-Gln-Pro-Pro-Gly-Leu-Lys-Val-Trp-Ser-Asp-Pro-Nap
(SEQ. ID NO: 51)

FIG. 51

Gln-Pro-Pro-Gly-Leu-Lys-Val-Trp-Ser-Asp-Pro-Nap
(SEQ. ID NO: 52)

FIG. 52 pGlu-Pro-Pro-Gly-Leu-Lys-Val-Trp-Ser-Asp-Pro-Nap
(SEQ. ID NO: 53)

FIG. 53

Ala-Gly-Ile-Val-Gln-Glu-Asp-Val-Gln-Pro-Pro-Gly-Leu-Lys-Val-Trp-Ser-Asp-Pro-Trp
(SEQ. ID NO: 54)

FIG. 54

Asp-Val-Gln-Pro-Pro-Gly-Leu-Lys-Val-Trp-Ser-Asp-Pro-Trp
(SEQ. ID NO: 55)

FIG. 55

Val-Gln-Pro-Pro-Gly-Leu-Lys-Val-Trp-Ser-Asp-Pro-Trp
(SEQ. ID NO: 56)

FIG. 56 pGlu-Glu-Asp-Val-Gln-Pro-Pro-Gly-Leu-Lys-Val-Trp-Ser-Asp-Pro-Trp
(SEQ. ID NO: 57)

FIG. 57

Gln-Pro-Pro-Gly-Leu-Lys-Val-Trp-Ser-Asp-Pro-Trp
(SEQ. ID NO: 58)

FIG. 58 pGlu-Pro-Pro-Gly-Leu-Lys-Val-Trp-Ser-Asp-Pro-Trp
(SEQ. ID NO: 59)

FIG. 59

Asp-Val-Gln-Pro-Pro-Gly-Leu-Lys-Val-Asp-dTrp-Ser-Asp-Pro-Trp
(SEQ. ID NO: 60)

Alignment of Phoenixin (1-20) (in box), Phoenixin (7-20) (in ``\_\_``) & Phoenixin (7-21) (in ``\_\_.``) between different species of prepro-protein

| | | | | | |
|---|---|---|---|---|---|
| Human | FGGFISLIGA | AFYPIYFRPL | MRLEEYKKEQ | AINRAGIVQE | DVQPPGLKVW SDPFGRK (SEQ. ID NO: 61) |
| Mouse | FGGFISMVGA | AFYPIYFRPL | LRLEEYQKEQ | AVNRAGIVQE | DVQPPGLKVW SDPFGRK (SEQ. ID NO: 62) |
| Rat | FGGFISMVGA | AFYPIYFRPL | LRLEEYQKEQ | AVNRAGIVQE | DVQPPGLKVW SDPFGRK (SEQ. ID NO: 63) |
| Pig | FGGFISLIGA | AFYPIYFRPL | MRLEEYQKEQ | AINRAGVVQE | DVQPPGLKVW SDPFGRK (SEQ. ID NO: 64) |
| Bovine | FGGFISLIGA | AFYPIYFRPL | MRLEEYKKEQ | AINRAGIVQE | DVQPPGLKVW SDPFGRK (SEQ. ID NO: 65) |
| Canis | | AFYPIYFRPL | LLPEEYQKEQ | AVNRAGIIQE | DVQPPGLKVW SDPFGRK (SEQ. ID NO: 66) |

PHOENIXIN PEPTIDES

This United States Patent Application is a continuation of U.S. patent application Ser. No. 14/119,866, filed Nov. 23, 2013, now U.S. Pat. No. 9,018,350, issued Apr. 28, 2015, which is the United States National Stage of International Patent Cooperation Treaty Patent Application No. PCT/US2012/039743, filed May 25, 2012, which claims the benefit of U.S. Provisional Patent Application No. 61/519,746, filed May 28, 2011, and U.S. Provisional Patent Application No. 61/519,747, filed May 26, 2011, each hereby incorporated by reference herein.

This United States Continuation Patent Application includes the material contained in the Sequence Listing created May 25, 2012 attached as a text file of 24 KB, hereby incorporated by reference herein.

I. TECHNICAL FIELD

Human phoenixin peptides, analogs and mimetics useful in production of anti-phoenixin antibodies, diagnostic screening and assays, and in modulating cellular concentration of cAMP, and methods of regulating, or treatment of disorders benefited by peptides capable of regulating, cAMP concentration in cells, modulating hypertension cardiovascular function, modulating gonadotrophs and gastric emptying.

II. BACKGROUND

The human propeptide Swiss-Prot: Q8N5G0 (also referred to as "Q8N5G0") including 168 amino acids as shown in FIG. 1 (SEQ. ID NO: 1) may be processed to obtain peptide forms which have been shown to modulate cell homeostasis of cardiovascular response, blood pressure, gastric emptying, and smooth muscle response.

However, all the processed forms of the human propeptide Q8N5G0 have not yet been fully identified or described and active chemically synthesized peptides having a reduced number of resides, greater stability or having greater activity over those known prior to the instant invention would be useful for: the production of polyclonal and monoclonal antibodies; diagnostic screening and assays; modulation of biochemical pathways; regulating concentration of cAMP or $Ca^{2+}$ in cells, smooth muscle response, gastric emptying; or treatment of disorders treatable with peptides which can modulate concentration of cAMP or $Ca^{2+}$ in cells, smooth muscle response, gastric emptying, or the like.

II. SUMMARY OF THE INVENTION

Accordingly a broad object of the invention can be to provide novel purified and isolated native peptides or chemically synthesized purified and isolated peptides (also referred to as the "phoenixin peptides") each corresponding to a portion, or providing in whole or in part a mimetic, of the human propeptide Q8N5G0) comprising 168 amino acids as shown in FIG. 1 (SEQ. ID NO: 1)(or similar propeptide of other species as shown in FIG. 71 (SEQ. ID NOS: 61 through 66)(individually and collectively referred to herein as the "phoenixin propeptide"). Native phoenixin peptides can be identical between species such as human, mouse, rat, pig, bovine, and canis. The purified and isolated native phoenixin propeptide and chemically synthesized isolated phoenixin peptides can be useful in regulating one or more of: production of cAMP in cells, homeostasis of cardiovascular responses, blood pressure, gastric emptying, and smooth muscle response, or useful for treatment of disorders that are benefited by regulation one or more of: production of cAMP in cells, homeostasis of cardiovascular responses, blood pressure, gastric emptying, and smooth muscle response.

Another broad object of the invention can be to provide chemically synthesized purified and isolated phoenixin peptides soluble and sufficiently stable in aqueous solutions, tissues, tissue homogenates, cell cultures, eluted fractions containing components thereof, or the like, useful screening assays and diagnostic procedures related to determination of one or more of: levels of phoenixin propeptides, levels of native phoenixin peptides resulting from processing of human, bovine, rat, mouse, pig, or dog phoenixin propeptide, levels of chemically synthesized phoenixin peptides, or the like.

Another broad object of the invention can be to provide purified and isolated chemically synthesized phoenixin peptides which can be utilized for the production of polyclonal and monoclonal antibodies which bind one or more of: human, bovine, rat, mouse, pig, dog, or other phoenixin propeptide, processed foams of human phoenixin propeptide, native fragments of phoenixin propeptide, or chemically synthesized purified and isolated phoenixin peptides.

Another broad object of the invention can be to provide purified and isolated phoenixin peptides which have similar function, similar or new and unexpectedly greater activity or specificity, or both, with respect to the substrates bound as compared to prior known peptides and confer such function, activity or specificity in a form which can as to certain embodiments omit one or more amino acid residues from known peptides and which confer a wide variety of advantages as to ease of production, increased potency, reduced cost, solubility, stability, or the like.

Another broad object of the invention can be to provide kits including one or more purified and isolated phoenixin peptides and which may further include antibodies raised to one or more phoenixin peptides useful in one or more of: radio-immunoassays ("RIA"), enzyme-linked immunosorbent assay ("ELISA"), or enzyme immunoassay ("EIA"), or the like, of tissue or cell homogenates or eluted fractions resulting from purification and isolation protocols using gel filtration, ion exchange chromatography, reverse phase chromatography, or the like, and for the immunohistochemical analysis of tissues, or as standards for chromatography or mass spectroscopy, or useful in screening and research methods for the determination of specific analogs, agonists, antagonists, partial mimetics, and agents that modulate their production, metabolism, and disposition.

Another broad object of the invention can be a method of regulating signal transduction in cells wherein an effective amount or therapeutic amount of one or more purified and isolated phoenixin peptides can be contacted with cells or otherwise administered to modulate or increase the production of cAMP or $Ca^{2+}$, or both, or to treat disorders related to deregulation of signal transduction in cells, tissues or animals.

Naturally, further objects of the invention are disclosed throughout other areas of the specification, drawings, photographs, and claims.

III. A BRIEF DESCRIPTION OF THE DRAWINGS

FIG. 1 shows the sequence of human cospeptin prepropeptide (Q8N5G0) residues 1-168 (SEQ. ID NO: 1).

FIG. 2 shows the sequence of phoenixin (1-20) (SEQ. ID NO: 2) which corresponds to the sequence of human cospeptin prepropeptide residues 146-165.

FIG. 3 shows the sequence phoenixin (7-21) (SEQ. ID NO: 3) which corresponds to the sequence of human cospeptin prepropeptide residues 152-166.

FIG. 4 shows the sequence of phoenixin (7-20) (SEQ. ID NO: 4) which corresponds to the sequence of human cospeptin prepropeptide residues 152-165.

FIG. 5 shows the sequence of phoenixin (9-21) (SEQ. ID NO: 5) which corresponds to the sequence of human cospeptin prepropeptide residues 154-166.

FIG. 6 shows the sequence of phoenixin (8-20) (SEQ. ID NO: 6) which corresponds to the sequence of human cospeptin prepropeptide residues 153-165.

FIG. 7 shows the sequence of phoenixin (1-20) amide (SEQ. ID NO: 7) which corresponds to the sequence of human cospeptin prepropeptide residues 146-165 and having a C-terminal amide.

FIG. 8 shows the sequence of phoenixin (8-20) amide (SEQ. ID NO: 8) which corresponds to the sequence of human cospeptin prepropeptide residues 153-165 and having a C-terminal amide.

FIG. 9 shows the sequence of phoenixin (7-20) amide (SEQ. ID NO: 9) which corresponds to the sequence of human cospeptin prepropeptide residues 152-165 and having a C-terminal amide.

FIG. 10 shows the sequence of pGlu-phoenixin (6-20) amide (SEQ. ID NO: 10) which corresponds to the sequence of human cospeptin prepropeptide residues 151-165 and having an N-terminal pyroglutamic acid and C-terminal amide.

FIG. 11 shows the sequence of phoenixin (9-20) amide (SEQ. ID NO: 11) which corresponds to the sequence of human cospeptin prepropeptide residues 154-165 and having a C-terminal amide.

FIG. 12 shows the sequence of pGlu-phoenixin (9-20) amide (SEQ. ID NO: 12) which corresponds to the sequence of human cospeptin prepropeptide residues 155-165 and having an N-terminal pyroglutamic acid and having a C-terminal amide.

FIG. 13 shows the sequence of phoenixin (1-20) methylamide (SEQ. ID NO: 13) which corresponds to the sequence of human cospeptin prepropeptide residues 146-165 and having a C-terminal methylamide.

FIG. 14 shows the sequence of phoenixin (8-20) methylamide (SEQ. ID NO: 14) which corresponds to the sequence of human cospeptin prepropeptide residues 153-165 and having a C-terminal methylamide.

FIG. 15 shows the sequence of phoenixin (7-20) methylamide (SEQ. ID NO: 15) which corresponds to the sequence of human cospeptin prepropeptide residues 152-165 and having a C-terminal methylamide.

FIG. 16 shows the sequence of p-glu phoenixin (6-20) methylamide (SEQ. ID NO: 16) which corresponds to the sequence of human cospeptin prepropeptide residues 151-165 and having an N-terminal pyroglutamic acid and a C-terminal methylamide.

FIG. 17 shows the sequence of phoenixin (9-20) methylamide (SEQ. ID NO: 17) which corresponds to the sequence of human cospeptin prepropeptide residues 154-165 and having a C-terminal methylamide.

FIG. 18 shows the sequence of pGlu-phoenixin (9-20) methylamide (SEQ. ID NO: 18) which corresponds to the sequence of human cospeptin prepropeptide residues 155-165 and having a N-terminal pyroglutamic acid and having a C-terminal methylamide.

FIG. 19 shows the sequence of phoenixin (1-20) ethylamide (SEQ. ID NO: 19) which corresponds to the sequence of human cospeptin prepropeptide residues 146-165 and having a C-terminal ethylamide.

FIG. 20 shows the sequence of phoenixin (8-20) ethylamide (SEQ. ID NO: 20) which corresponds to the sequence of human cospeptin prepropeptide residues 153-165 and having a C-terminal ethylamide.

FIG. 21 shows the sequence of phoenixin (7-20) ethylamide (SEQ. ID NO: 21) which corresponds to the sequence of human cospeptin prepropeptide residues 152-165 and having a C-terminal ethylamide.

FIG. 22 shows the sequence of pGlu-phoenixin (6-20) ethylamide (SEQ. ID NO: 22) which corresponds to the sequence of human cospeptin prepropeptide residues 151-165 and having a N-terminal pyroglutamic acid and having a C-terminal ethylamide.

FIG. 23 shows the sequence of phoenixin (9-20) ethylamide (SEQ. ID NO: 23) which corresponds to the sequence of human cospeptin prepropeptide residues 154-165 and having a C-terminal ethylamide.

FIG. 24 shows the sequence of pGlu-phoenixin (9-20) ethylamide (SEQ. ID NO: 24) which corresponds to the sequence of cospeptin prepropeptide residues 155-165 and having an N-terminal pyroglutamic acid and having a C-terminal ethylamide.

FIG. 25 shows the sequence of phoenixin (7-20, dValine (8)) amide (SEQ. ID NO: 25) which corresponds to the sequence of human cospeptin prepropeptide residues 152-165 and having a d-form of valine at residue 153 and having a C-terminal amide.

FIG. 26 shows the sequence of phoenixin (7-20, dProline (10)) amide (SEQ. ID NO: 26) which corresponds to the sequence of human cospeptin prepropeptide residues 152-165 and having a d-form of proline at residue 155 and having a C-terminal amide.

FIG. 27 shows the sequence of phoenixin (7-20, dProline (11)) amide (SEQ. ID NO: 27) which corresponds to the sequence of human cospeptin prepropeptide residues 152-165 and having a d-form of proline at residue 156 and having a C-terminal amide.

FIG. 28 shows the sequence of phoenixin (7-20, dAlanine (12) amide (SEQ. ID NO: 28) which corresponds to the sequence of human cospeptin prepropeptide residues 152-165 and having a d-form of alanine in substitution of the glycine at residue 157 and having a C-terminal amide.

FIG. 29 shows the sequence of phoenixin (7-20, dLeucine (13)) amide (SEQ. ID NO: 29) which corresponds to the sequence of human cospeptin prepropeptide residues 152-165 and having a d-form of leucine at residue 158 and having a C-terminal amide.

FIG. 30 shows the sequence of phoenixin (7-20, dValine (15)) amide (SEQ. ID NO: 30) which corresponds to the sequence of human cospeptin prepropeptide residues 152-165 and having a d-form of valine at residue 160 and having a C-terminal amide.

FIG. 31 shows the sequence of phoenixin (7-20, dTryptophan (16)) amide (SEQ. ID NO: 31) which corresponds to the sequence of human cospeptin prepropeptide residues 152-165 and having a d-form of tryptophan at residue 161 and having a C-terminal amide.

FIG. 32 shows the sequence of phoenixin (7-20, dProline (19)) amide (SEQ. ID NO: 32) which corresponds to the sequence of human cospeptin prepropeptide residues 152-165 and having a d-form of proline at residue 164 and having a C-terminal amide.

FIG. 33 shows the sequence of phoenixin (7-20, dPhenylalanine (20)) amide (SEQ. ID NO: 33) which corresponds to the sequence of human cospeptin prepropeptide residues 152-165 and having a d-form of phenylalanine at residue 165 and having a C-terminal amide.

Figure 61:
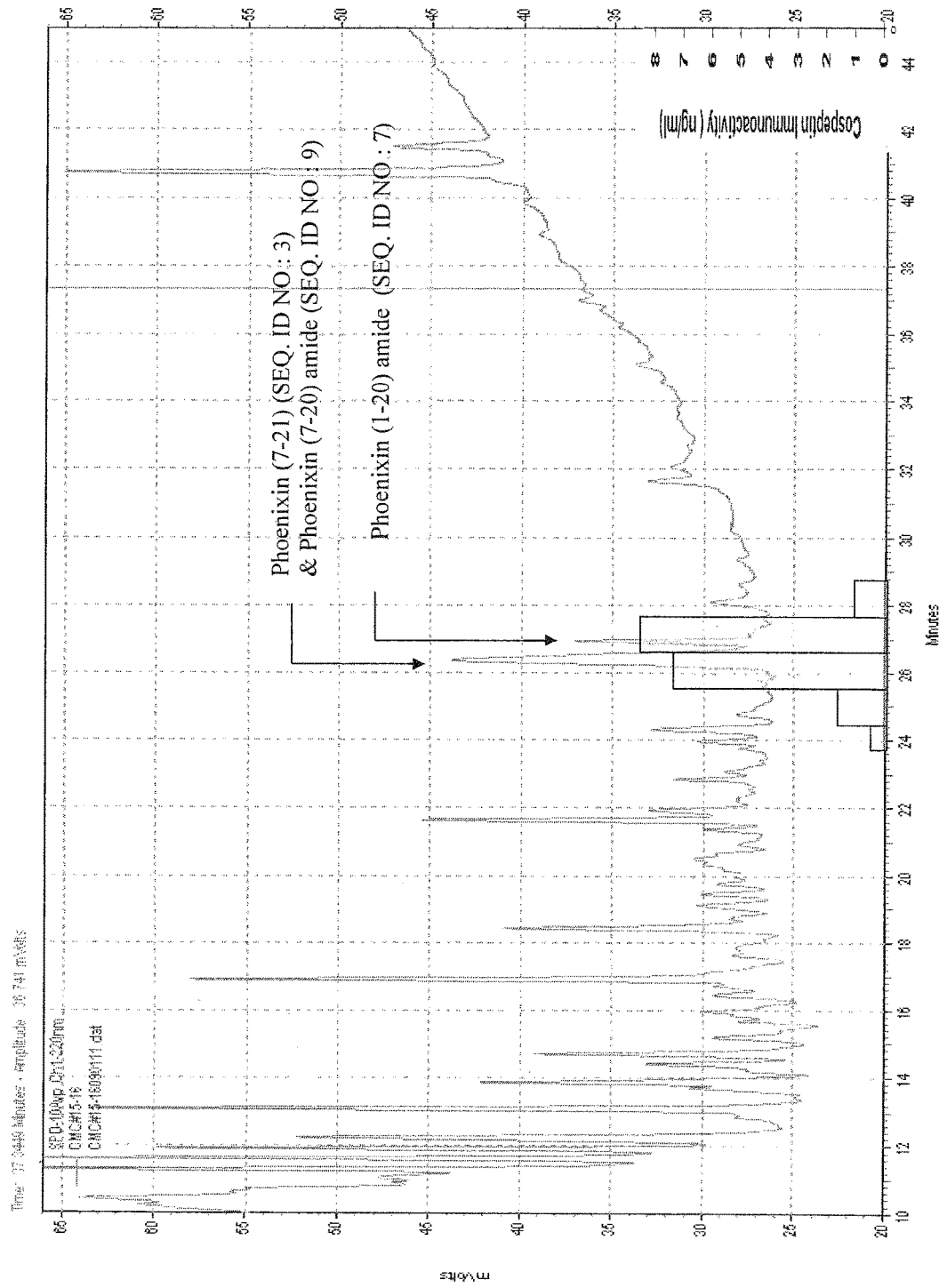

FIG. 34 shows the sequence of phoenixin (7-20, Tic(20)) amide (SEQ. ID NO: 34) which corresponds to the sequence of human cospeptin prepropeptide residues 152-165 and having a 1,2,3,4-tetrahydroisoquinoline-3-carboxylic acid at residue 165 in substitution of the 1-form of phenylalanine and having a C-terminal amide.

FIG. 35 shows the sequence of phoenixin (1-20, dAlanine (1)) amide (SEQ. ID NO: 35) which corresponds to the sequence of human cospeptin prepropeptide residues 146-165 and having a d-form of alanine at residue 146 and having a C-terminal amide.

FIG. 36 shows the sequence of phoenixin (1-20, dAlanine (2)) amide (SEQ. ID NO: 36) which corresponds to the sequence of cospeptin prepropeptide residues 146-165 and having a d-form of alanine at residue 147 in substitution for the 1-form glycine and having a C-terminal amide.

FIG. 37 shows the sequence of phoenixin (1-20, dValine (4)) amide (SEQ. ID NO: 37) which corresponds to the sequence of human cospeptin prepropeptide residues 146-165 and having a d-form of valine at residue 149 and having a C-terminal amide.

FIG. 38 shows the sequence of phoenixin (1-20, dValine (8)) amide (SEQ. ID NO: 38) which corresponds to the sequence of human cospeptin prepropeptide residues 146-165 and having a d-form of valine at residue 153 and having a C-terminal amide.

FIG. 39 shows the sequence of phoenixin (1-20, dSerine (17)) amide (SEQ. ID NO: 39) which corresponds to the sequence of human cospeptin prepropeptide residues 146-165 and having a d-form of serine at residue 162 and having a C-terminal amide.

FIG. 40 shows the sequence of phoenixin (1-20, dProline (19)) amide (SEQ. ID NO: 40) which corresponds to the sequence of human cospeptin prepropeptide residues 146-165 and having a d-form of proline at residue 164 and having a C-terminal amide.

FIG. 41 shows the sequence of phoenixin (1-20, dPhenylalanine (20)) amide (SEQ. ID NO: 41) which corresponds to the sequence of human cospeptin prepropeptide residues 146-165 and having a d-form of phenylalanine at residue 165 and having a C-terminal amide.

FIG. 42 shows the sequence of phoenixin acetyl (1-20) amide (SEQ. ID NO: 42) which corresponds to the sequence of human cospeptin prepropeptide residues 146-165 and having an N-terminal acetyl and having a C-terminal amide.

FIG. 43 shows the sequence of phoenixin acetyl (8-20) amide (SEQ. ID NO: 43) which corresponds to the sequence of human cospeptin prepropeptide residues 153-165 and having an N-terminal acetyl and having a C-terminal amide.

FIG. 44 shows the sequence of phoenixin acetyl (7-20) amide (SEQ. ID NO: 44) which corresponds to the sequence of cospeptin prepropeptide residues 152-165 and having an N-terminal acetyl and having a C-terminal amide.

FIG. 45 shows the sequence of phoenixin formyl (1-20) amide (SEQ. ID NO: 45) which corresponds to the sequence of human cospeptin prepropeptide residues 146-165 and having an N-terminal formyl and having a C-terminal amide.

FIG. 46 shows the sequence of phoenixin formyl (6-20) amide (SEQ. ID NO: 46) which corresponds to the sequence of human cospeptin prepropeptide residues 151-165 and having an N-terminal formyl and having a C-terminal amide.

FIG. 47 shows the sequence of phoenixin formyl (7-20) amide (SEQ. ID NO: 47) which corresponds to the sequence of human cospeptin prepropeptide residues 152-165 and having an N-terminal formyl and having a C-terminal amide.

FIG. 48 shows the sequence of phoenixin (1-19) napthalene (SEQ. ID NO: 48) which corresponds to the sequence of human cospeptin prepropeptide residues 146-164 and having a C-terminal naphthalene.

FIG. 49 shows the sequence of phoenixin (7-19) napthalene (SEQ. ID NO: 49) which corresponds to the sequence of human cospeptin prepropeptide residues 152-164 and having a C-terminal naphthalene.

FIG. 50 shows the sequence of phoenixin (8-19) napthalene (SEQ. ID NO: 50) which corresponds to the sequence of human cospeptin prepropeptide residues 153-164 and having a C-terminal naphthalene.

FIG. 51 shows the sequence of pGlu-Phoenixin (6-19) napthalene (SEQ. ID NO: 51) has a sequence located the primary sequence of human cospeptin prepropeptide residues 151-164, pyroglutamic acid at N-terminal and having a C-terminal naphthalene.

FIG. 52 shows the sequence of phoenixin (9-19) napthalene (SEQ. ID NO: 52) which corresponds to the sequence of human cospeptin prepropeptide residues 154-164 and having a C-terminal naphthalene.

FIG. 53 shows the sequence of pGlu-phoenixin (9-19) napthalene (SEQ. ID NO: 53) which corresponds to the sequence of human cospeptin prepropeptide residues 155-164 and having a pyroglutamic acid at the N-terminal and having a C-terminal naphthalene.

FIG. 54 shows the sequence of Phoenixin (1-20, tryptophan (20)) (SEQ. ID NO: 54) which corresponds to the sequence of human cospeptin prepropeptide residues 146-165 and having the phenylalanine at residue 165 substituted with tryptophan.

FIG. 55 shows the sequence of phoenixin (7-20, tryptophan (20)) (SEQ. ID NO: 55) which corresponds to the sequence of human cospeptin prepropeptide residues 152-165 and having the phenylalanine at residue 165 to be substituted with tryptophan.

FIG. 56 shows the sequence of phoenixin (8-20, tryptophan (20)) (SEQ. ID NO: 56) which corresponds to the sequence of human cospeptin prepropeptide residues 153-165 and having the phenylalanine at residue 165 to be substituted with tryptophan.

FIG. 57 shows the sequence of pGlu-phoenixin (5-20, tryptophan (20)) (SEQ. ID NO: 57) which corresponds to the sequence of human cospeptin prepropeptide residues 151-165, pyroglutamic acid at N-terminal and having the phenylalanine at residue 165 to be substituted with tryptophan.

FIG. 58 shows the sequence of phoenixin (9-20, tryptophan (20)) (SEQ. ID NO: 58) which corresponds to the sequence of human cospeptin prepropeptide residues 154-165 and having the phenylalanine at residue 165 to be substituted with tryptophan.

FIG. 59 shows the sequence of pGlu-phoenixin (9-20, tryptophan (20)) (SEQ. ID NO: 59) which corresponds to the sequence of human cospeptin prepropeptide residues 155-165, pyroglutamic acid at N-terminal and having the phenylalanine at residue 165 to be substituted with tryptophan.

FIG. 60 shows the sequence of phoenixin (7-20, dTryptophan (11) tryptophan (20)) (SEQ. ID NO: 60) which corresponds to the sequence of human cospeptin prepropeptide residues 152-165 and having the D-isoform of tryptophan at residue 161 and having the phenylalanine at residue 165 to be substituted with tryptophan.

FIG. 61 is a first RP-HPLC separation plot which shows the elution of immunoreactive peptides (peaks above the baseline) resulting from application of RP-HPLC to the immunoreactive fractions obtained from size fractionation purification of rat tissue homogenates.

Figure 62:
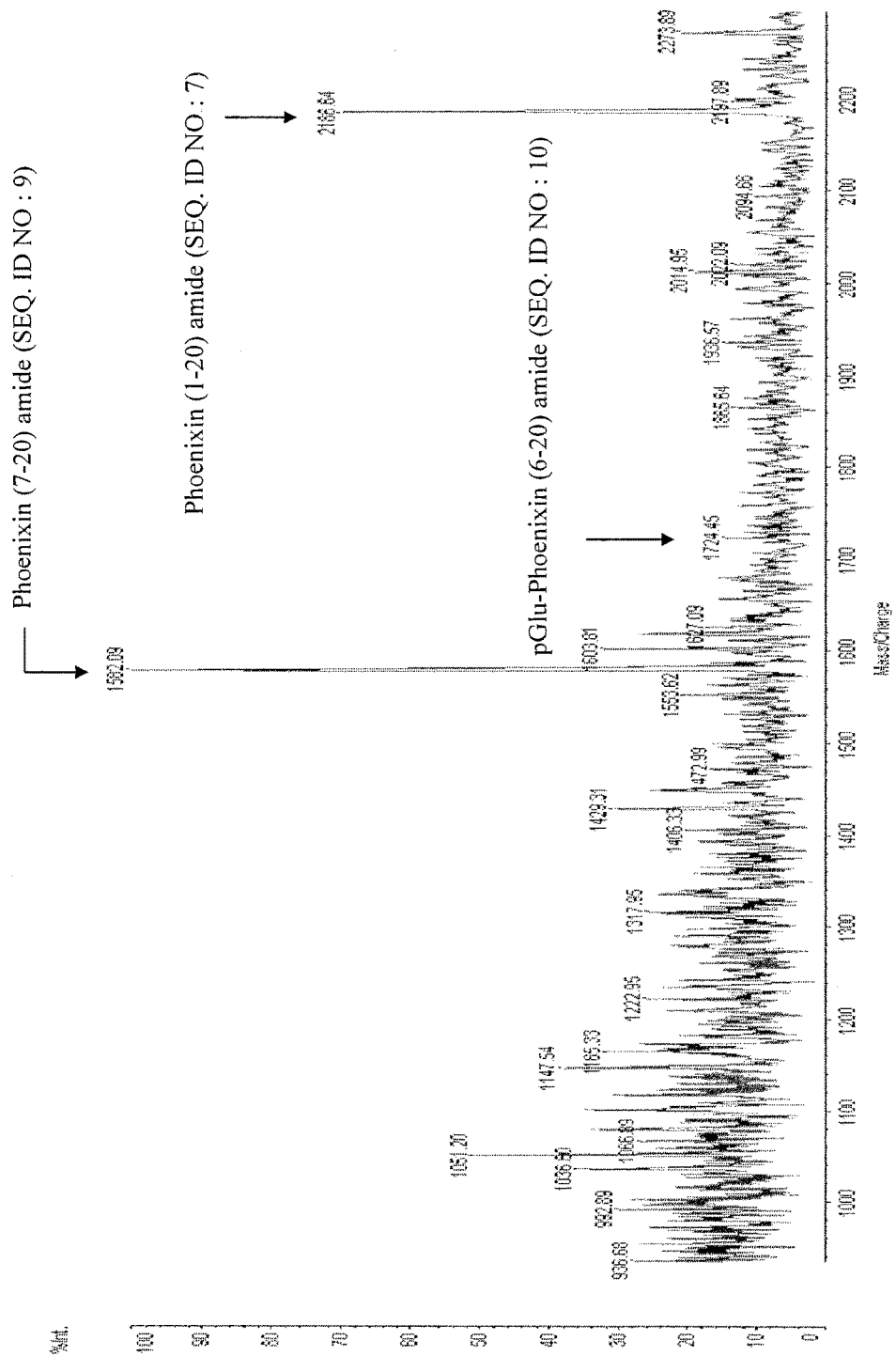

FIG. 62 is a mass spectrum profile resulting from mass spectroscopy of the fraction including the peak eluting at about 26.5 minutes in the first RP-HPLC separation of FIG. 61.

Figure 63:
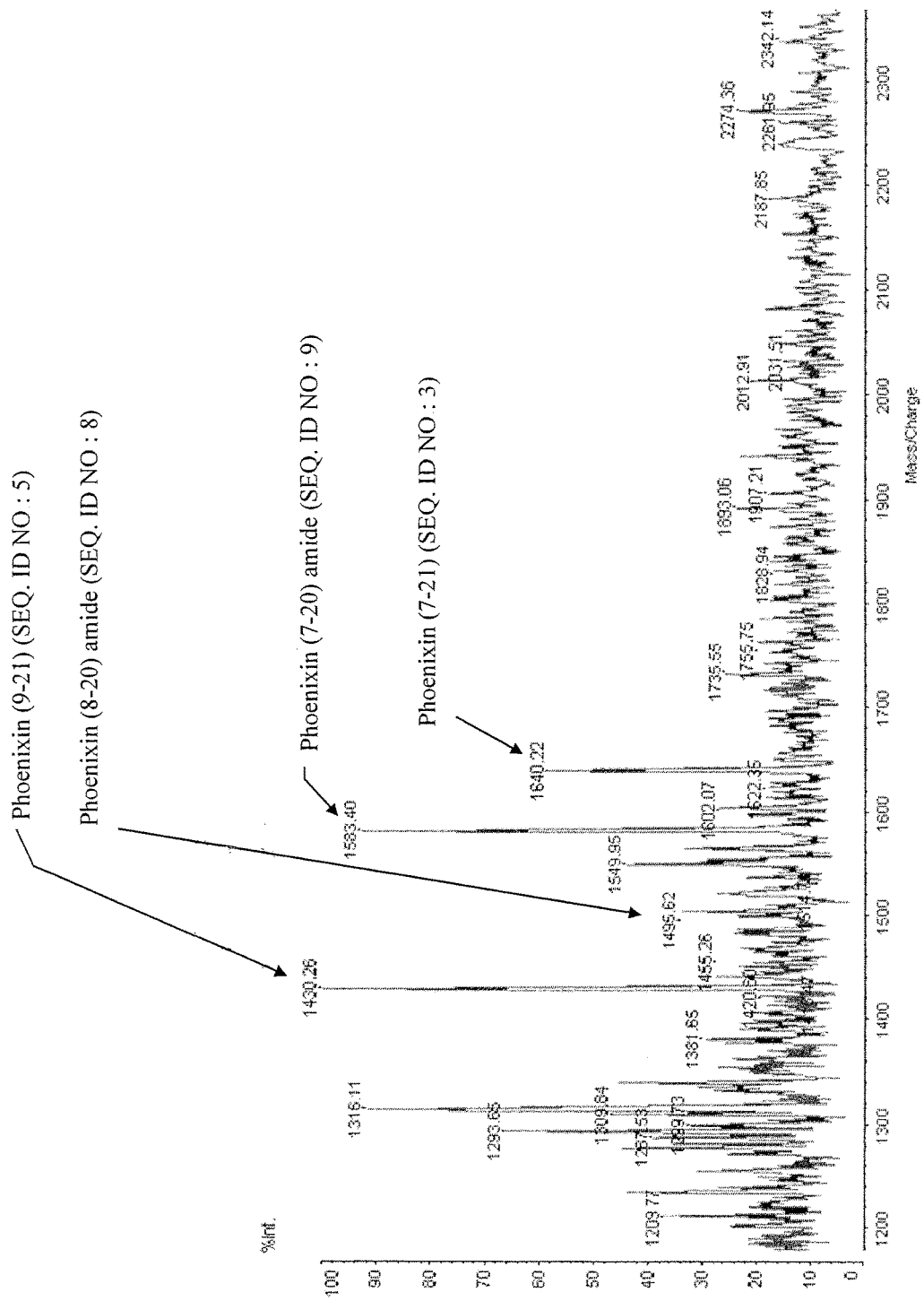

FIG. 63 is a mass spectrum profile resulting from mass spectroscopy in high voltage mode of the fraction eluted fraction at about 27 minutes in the first RP-HPLC separation of FIG. 61.

Figure 64:
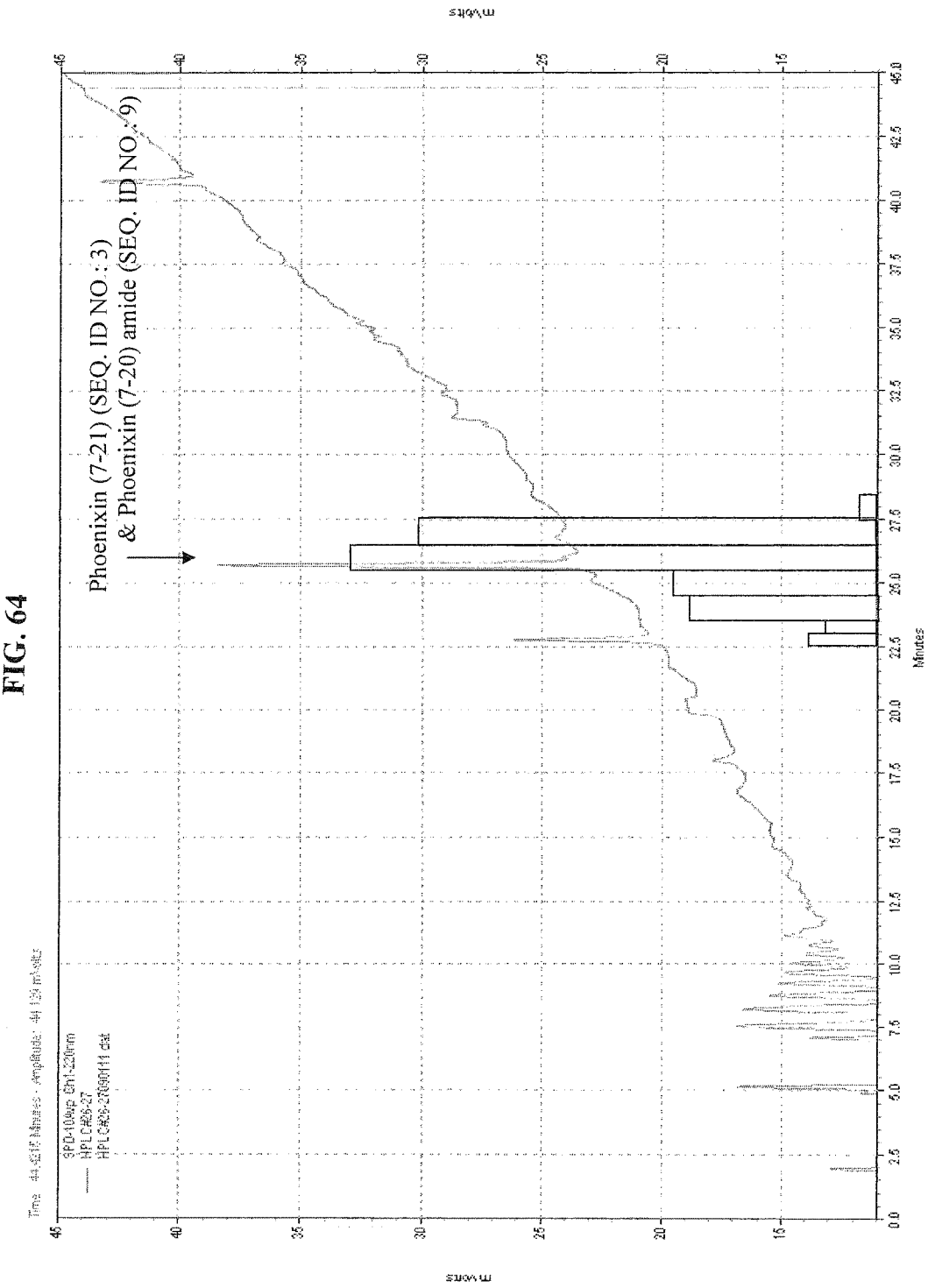

FIG. 64 is a second RP-HPLC separation plot which shows the elution of peptides (peaks above the baseline) resulting from application of RP-HPLC to the immunoreactive fractions obtained by the above described first RP-HPLC separation of FIG. 61.

Figure 65:
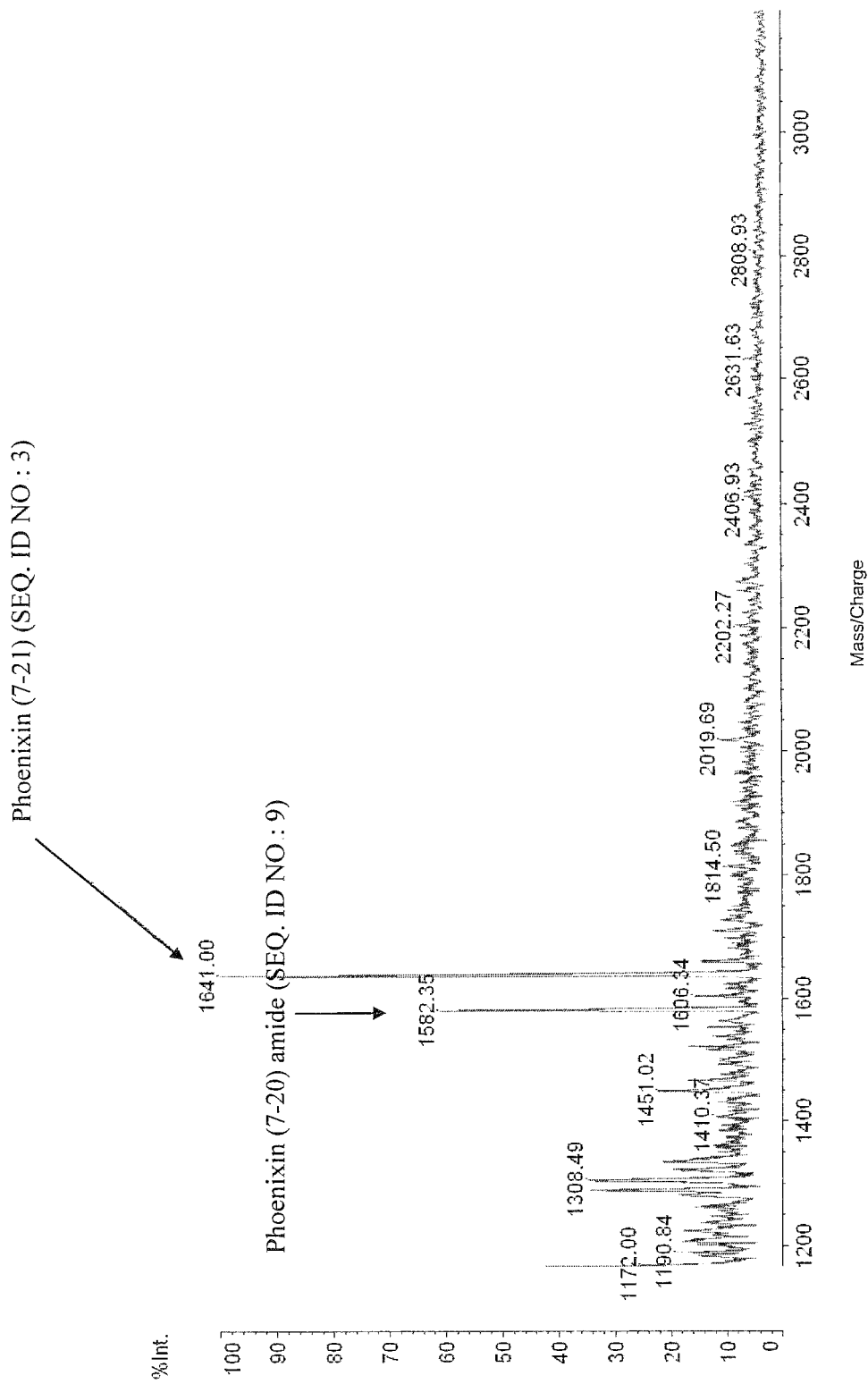

FIG. 65 is a mass spectrum profile resulting from mass spectroscopy of the fraction including the peak eluting at about 26.5 minutes in the second RP-HPLC separation of FIG. 64.

Figure 66A:

FIG. 66A is an image of a tissue section of rat medulla on a glass slide fixed and immunostained using the anti-phoenixin antibodies raised against AGIVQEDVQPPGLKVWSDPF-NH2 (SEQ. ID NO: 7) as shown in FIG. 7.

Figure 66B:
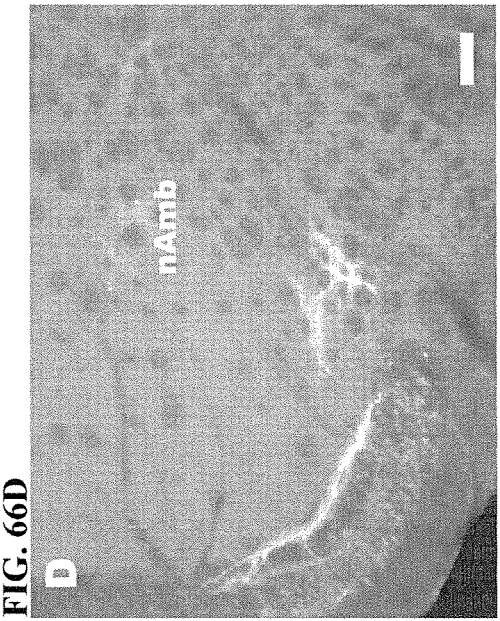

FIG. 66B is an image of a tissue section of rat medulla on a glass slide fixed and immunostained using the anti-phoenixin antibodies raised against AGIVQEDVQPPGLKVWSDPF-NH2 (SEQ. ID NO: 7) as shown in FIG. 7.

Figure 66C:
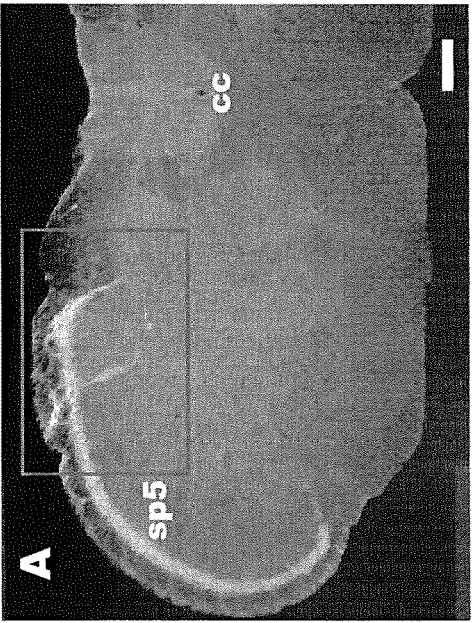

FIG. 66C is an image of a tissue section of rat medulla on a glass slide fixed and immunostained using the anti-phoenixin antibodies raised against AGIVQEDVQPPGLKVWSDPF-NH2 (SEQ. ID NO: 7) as shown in FIG. 7.

Figure 66D:
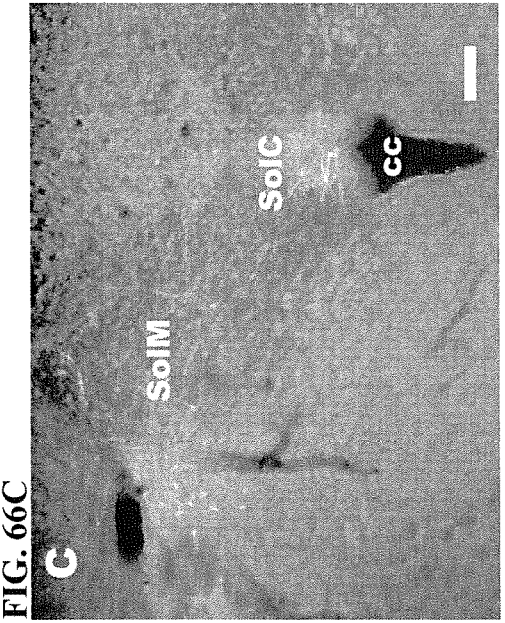

FIG. 66D is an image of a tissue section of rat medulla on a glass slide fixed and immunostained using the anti-phoenixin antibodies raised against AGIVQEDVQPPGLKVWSDPF-NH2 (SEQ. ID NO: 7) as shown in FIG. 7.

Figure 67B:
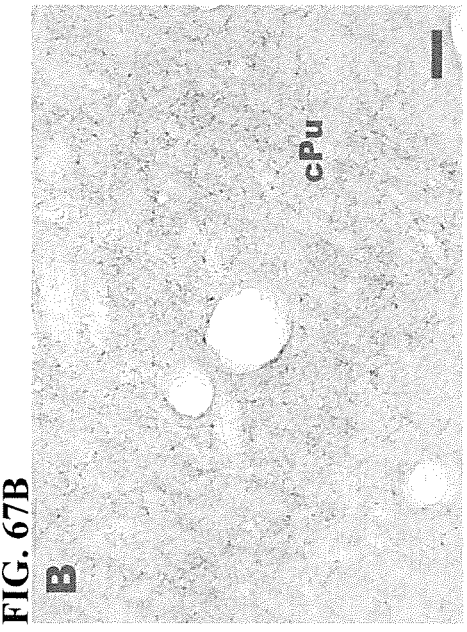
Figure 67D:
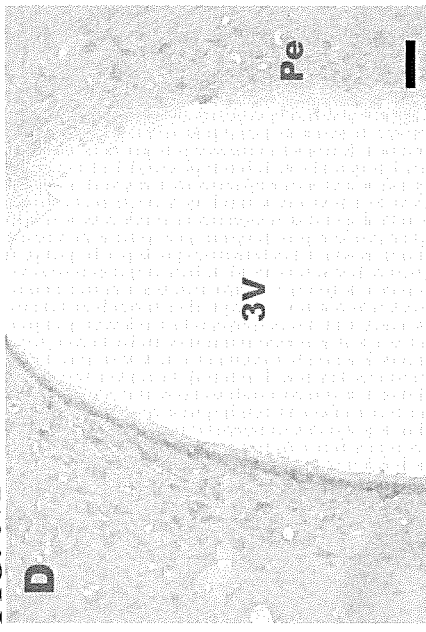
Figure 67A:
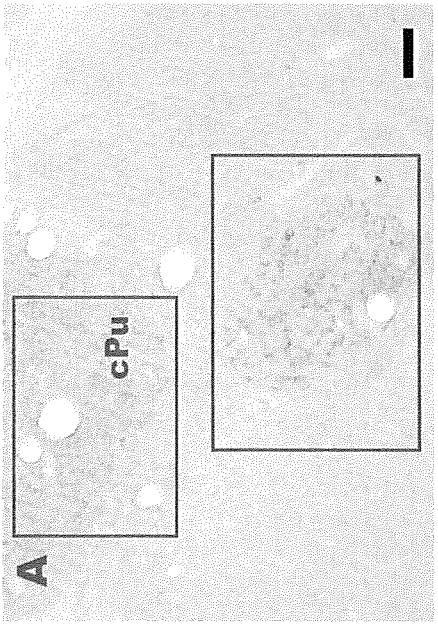

FIG. 67A is an image of a tissue section of rat forebrain on a glass slide fixed and immunostained using the anti-phoenixin antibodies raised against AGIVQEDVQPPGLKVWSDPF-NH2 (SEQ. ID NO: 7) shown in FIG. 7.

FIG. 67B is an image of a tissue section of rat forebrain on a glass slide fixed and immunostained using the anti-phoenixin antibodies raised against AGIVQEDVQPPGLKVWSDPF-NH2 (SEQ. ID NO: 7) shown in FIG. 7.

Figure 67C:
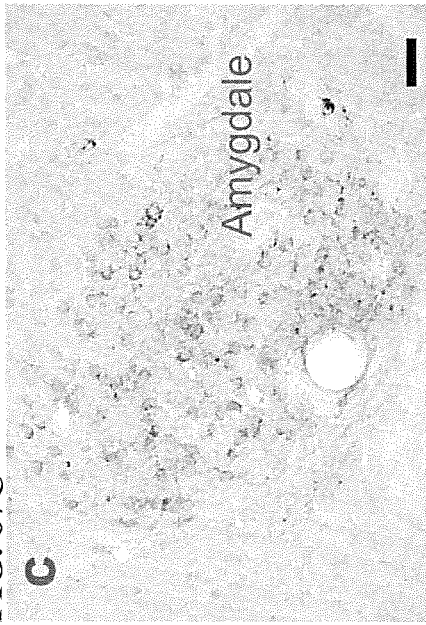

FIG. 67C is an image of a tissue section of rat forebrain on a glass slide fixed and immunostained using the anti-phoenixin antibodies raised against AGIVQEDVQPPGLKVWSDPF-NH2 (SEQ. ID NO: 7) shown in FIG. 7.

FIG. 67D is an image of a tissue section of rat forebrain on a glass slide fixed and immunostained using the anti-phoenixin antibodies raised against AGIVQEDVQPPGLKVWSDPF-NH2 (SEQ. ID NO: 7) shown in FIG. 7.

Figure 68C:
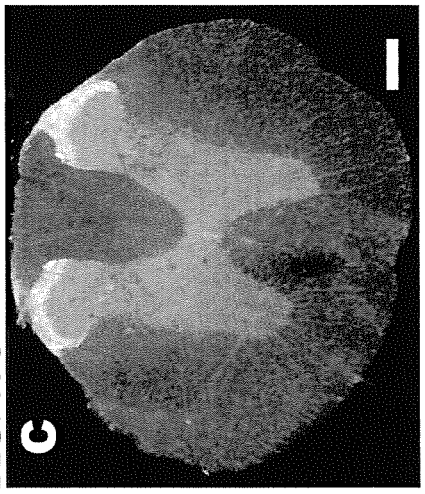
Figure 68F:
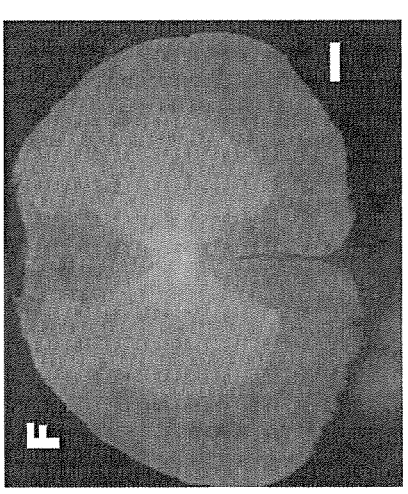
Figure 68B:
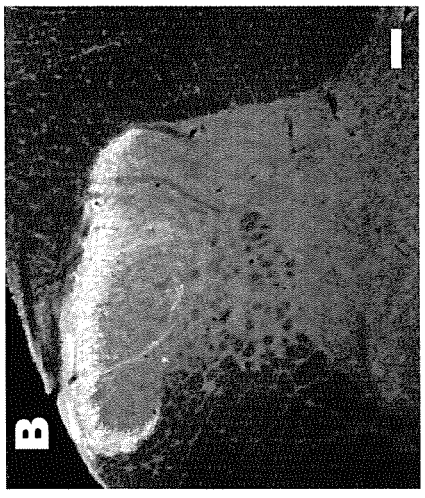
Figure 68E:
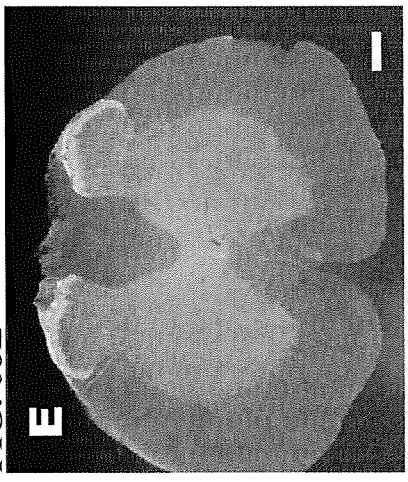
Figure 68A:

FIG. 68A is an image of a tissue section of rat spinal cord on glass slide fixed and immunostained using the anti-phoenixin antibodies raised against AGIVQEDVQPPGLKVWSDPF-NH2 (SEQ. ID NO: 7) showed in FIG. 7.

FIG. 68B is an image of a tissue section of rat spinal cord on a glass slide fixed and immunostained using the anti-phoenixin antibodies raised against AGIVQEDVQPPGLKVWSDPF-NH2 (SEQ. ID NO: 7) showed in FIG. 7.

FIG. 68C is an image of a tissue section of rat spinal cord on a glass slide fixed and immunostained using the anti-phoenixin antibodies raised against AGIVQEDVQPPGLKVWSDPF-NH2 (SEQ. ID NO: 7) showed in FIG. 7.

Figure 68D:
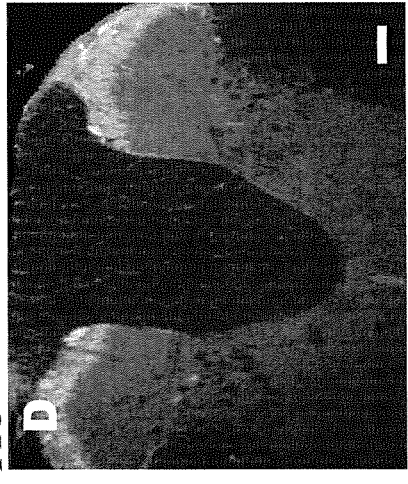

FIG. 68D is an image of a tissue section of rat spinal cord on a glass slide fixed and immunostained using the anti-phoenixin antibodies raised against AGIVQEDVQPPGLKVWSDPF-NH2 (SEQ. ID NO: 7) showed in FIG. 7.

FIG. 68E is an image of a tissue section of rat spinal cord on a glass slide fixed and immunostained using the anti-phoenixin antibodies raised against AGIVQEDVQPPGLKVWSDPF-NH2 (SEQ. ID NO: 7) showed in FIG. 7.

FIG. 68F is an image of a tissue section of rat spinal cord on a glass slide fixed and immunostained using the anti-phoenixin antibodies raised against AGIVQEDVQPPGLKVWSDPF-NH2 (SEQ. ID NO: 7) showed in FIG. 7.

Figure 69:
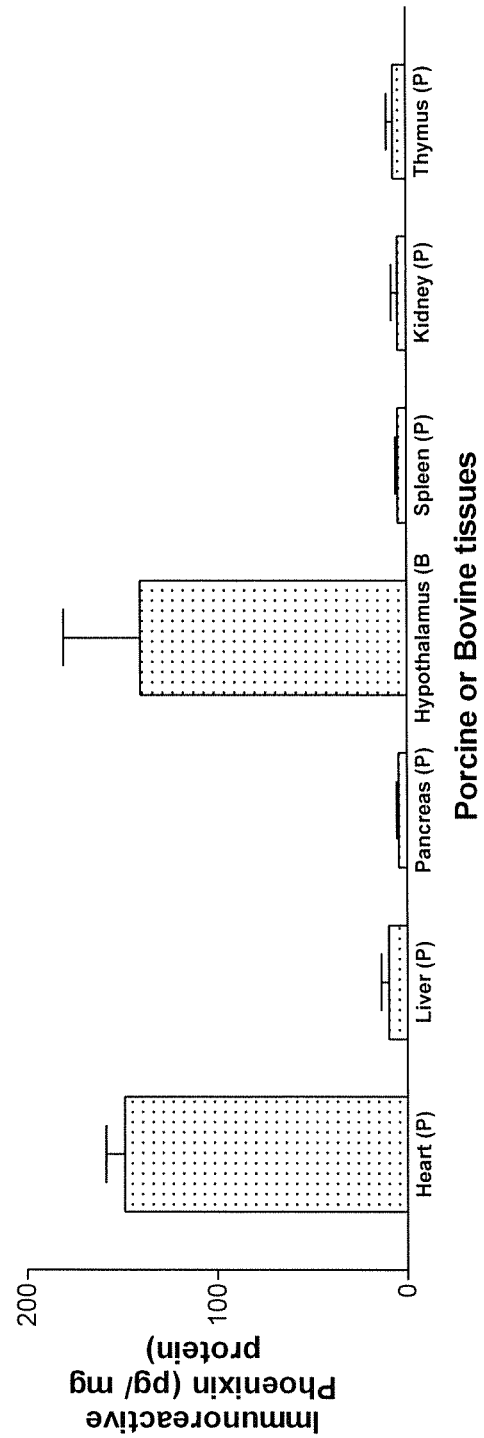

FIG. 69 is a bar graph which plots the tissue distribution and concentration of native phoenixin peptides corresponding to AGIVQEDVQPPGLKVWSDPF-NH2 (SEQ. ID NO: 7) and DVQPPGLKVWSDPF-NH2 (SEQ. ID NO: 9) as shown in FIG. 7 and FIG. 9.

Figure 70:
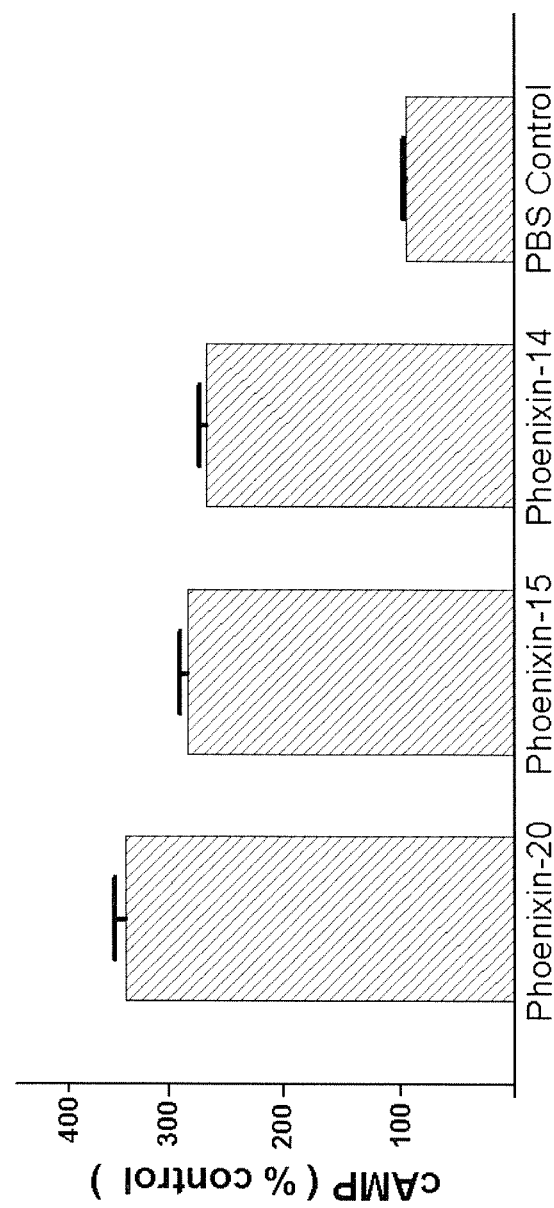

FIG. 70 is a bar graph compares the production of cAMP in rat pituitary cells challenged with AGIVQEDVQPPGLKVWSDPF-NH2 (SEQ. ID NO: 7) as shown in FIG. 7, DVQPPGLKVWSDPFG (SEQ. ID NO: 3) as shown in FIG. 3, DVQPPGLKVWSDPF-NH2 (SEQ. ID NO: 9) as shown in FIG. 9, and a phosphate buffered saline ("PBS") control.

FIG. 71 shows the alignment of the region of phoenixin (1-20), phoenixin (7-20), and phoenixin (7-21) in different species of animals. From the sequence alignment, the sequence of phoenixin (1-20) in the prepropeptides is identical between the species of human, bovine, rat, and mouse. The peptide of phoenixin (1-20) in the species of canis and pig have one residue difference which is a substitution of valine or isoleucine for the residue of isoleucine or valine.

IV. DETAILED DESCRIPTION OF THE PREFERRED EMBODIMENTS

As can be easily understood from this description, the basic concepts of the present invention may be embodied in a variety of ways. It involves methods of producing and using purified and isolated polypeptides and peptide mimetics which are ligands for protein coupled receptors in regulation of cellular function in gastrointestinal, cardiovascular, hypothalamus-pituitary axis, and central nervous system tissues.

Now referring primarily to FIG. 1, the human phoenixin propeptide (Q8N5G0) of 168 amino acids (SEQ. ID NO: 1) can be processed to various peptide forms including: AGIVQEDVQPPGLKVWSDPF (SEQ. ID NO: 2) 20 amino acid residues in length as shown in FIG. 2; DVQPPGLKVWSDPFG (SEQ. ID NO: 3) 15 amino acid residues in length as shown in FIG. 3; DVQPPGLKVWSDPF (SEQ. ID NO: 4) 14 amino acid residues in length as shown in FIG. 4, QPPGLKVWSDPFG (SEQ. ID NO: 5) 13 amino acid residues in length as shown in FIG. 5, and VQPPGLKVWSDPF (SEQ. ID NO: 6) 13 amino acid residues in length as shown in FIG. 6.

The native phoenixin peptides, as above described, may be in the form of a free acid at the carboxyl terminus or may be amidated in the form of AGIVQEDVQPPGLKVWSDPF-NH2 (SEQ. ID NO: 7) as shown in FIG. 7, VQPPGLKVWSDPF-NH2 (SEQ. ID NO: 8) as shown in FIG. 8, or as DVQPPGLKVWSDPF-NH2 (SEQ. ID NO: 9) as shown in FIG. 9.

Certain residues of the phoenixin peptides (whether free acid or amide) may be L-isoform amino acid or D-isoform amino acid. For example, DVQPPGLKVWSDPFG-NH2

(SEQ. ID NO: 9) as shown in FIG. 9, and DVQPPGLKVd-WSDPF-NH2 (SEQ. ID NO: 31) as shown in FIG. 31.

Phoenixin transcripts can be expressed in human tissues of the gastrointestinal tract, hypothalamus, medulla, forebrain, heart, pituitary, kidney, pancreas, liver, spleen, thymus, and other tissues.

Prediction of Phoenixin Sequences

A peptide library was designed from potential mono- or di-basic cleavage sites in about 100 known preprohormone phoenixin sequences. Candidates for peptide synthesis were selected based upon the expectation that the preprohormone phoenixin protein may be processed in-vivo at a monobasic residue such as Arg or Lys, dibasic residue pair such as Arg-Arg, a multibasic cleavage site, or the triplet Gly-Arg-Arg which upon proteolytic cleavage can generate the in-vivo processed forms of human phoenixin, or other forms suitable for antibody production for the capture of the processed forms of human phoenixin. The modeling resulted in the primary sequence of candidates from which the following were selected for chemical synthesis: AGIVQED-VQPPGLKVWSDPF (SEQ. ID NO: 2), DVQPPGLKVWS-DPFG (SEQ. ID NO: 3) and DVQPPGLKVWSDPF (SEQ. ID NO: 4).

Production of Phoenixin Peptides

Now referring primarily to FIGS. 2-60, once the primary sequence of SEQ. ID NO: 2, SEQ. ID NO: 3, and SEQ. ID NO: 4 were determined by modeling, the corresponding C-terminal free acid (SEQ ID. NOS: 2 through 6), C-terminal amide (SEQ ID NOS: 7 through 12), C-terminal methylamide (SEQ. ID NOS: 13 through 18), C-terminal ethylamide (SEQ. ID NOS: 19 through 24), D form amino acid peptides (SEQ. ID NOS: 24 through 41 and 60), N-terminal acetyl (SEQ. ID NOS: 42 through 44), N-terminal formyl (SEQ. ID NOS: 45-47), C-terminal naphthalene (SEQ. ID NOS: 48-50 and 52), and tryptophan substituted for phenylalanine (SEQ. ID. NOS: 54 through 60) peptides were chemically synthesized chemically using fluorenyloxymethylcarbonyl (FMOC) amino acids or tertbutyloxymethylcarbonyl (BOC) amino acids either with an automated peptide synthesizer, such as Ranin Instruments Symphony-Multiplex peptide synthesizer according to the manufacturer's protocol, or manually as understood by techniques well known to those skilled in the art. See also Solid Phase Peptide Synthesis: A practical approach, E. Atherton and R. C. Sheppard, IRL Press, Oxford, England, hereby incorporated by reference.

Certain phoenixin peptides modified to provide one or more of: N-terminal acetyl, N-terminal formyl, N-terminal pyroglutamic acid, C-terminal amide, C-terminal methyl amide, C-terminal ethylamide, C-terminal naphthalene, C-terminal tryptophan, substitution of one or more L isoform amino acid residues for the same D isoform amino acid can have one more of the advantages of being more stable, more soluble, or have a greater potency as compared to the corresponding original native peptide. See for example, Wei E. T et al., *Peptides*. 1998; 19(7):1183-90, hereby incorporated by reference.

The resulting mixture of polypeptides from the chemical synthesis can be purified and isolated from one another by reverse phase ("RP") high pressure liquid chromatography ("HPLC") using columns packed with silica having a pore of between 80 angstrom ("A") and 300 Å with any one of a C-4, C-8, or C-18 ligand attached. The columns were equilibrated with 0.1% trifluoroacetic acid in water at a flow rate dependent on column size, as would be understood by those having ordinary skill in the art. The synthetic peptide mixtures were applied to the reverse phase HPLC columns and eluted with 0.1% trifluoroacetic acid in acetonitrile using a gradient of about 0% to about 60% over a period of about 1 hour. Fractions were collected at about 0.5 minute intervals. Fractions were subsequently analyzed for homogeneity by re-application and elution from the reverse phase HPLC system, mass spectrometry, SDS-PAGE, or automated Edman degradation on a Perkin Elmer/Applied Biosystems Model 470A protein sequencer in accordance with the manufacturer's protocol.

The invention further encompasses purified and isolated peptides substantially similar to one or more of the phoenixin peptides shown in FIGS. 2-60 (SEQ. ID NOS: 2 through 60) which retain the function to modulate intracellular cyclic adenosine monophosphate ("cAMP") concentration in rat pituitary cells. As non-limiting examples, silent substitutions of residues wherein the replacement of the residue with structurally or chemically similar residue which does not significantly alter the structure, conformation, or activity of the polypeptide. Such silent substitutions are intended to fall within the scope of the claims which may be filed in a subsequent non-provisional patent application. As such, the invention and this description is understood to further include peptides related to SEQ. ID NOS: 2 through 60 wherein one or more residues is removed from either end or both ends, or from an internal region, or wherein one or more residues is added to either end or both ends, or to an internal location in a peptide, or peptides having chemical moieties or residues added for chemical or radiolabeling, such as, an added tyrosine for $^{125}$iodine labeling. Similarly, the N-terminus can be prepared as amino, acetyl, formyl, or left with a residual FMOC or BOC group intact. The C-terminus can be left bound to the resin, or cleaved as a carboxyl or an amide by choice of the corresponding 4-hydroxymethyl-phenylacetamidomethyl ("PAM") resin or 4-methylbenzhydrylamine hydrochloride salt ("MBHA") resin. The C-terminus can be modified to provide a methyl amide, ethyl amide, naphthalene, or other moiety.

Production of Anti-Phoenixin and Phoenixin Peptide Antibodies

Antibodies were raised against each of the chemically synthesized purified and isolated peptides corresponding to SEQ. ID NO: 3, SEQ. ID NO: 7, SEQ. ID NO: 9, SEQ. ID NO: 10 and SEQ. ID NO: 11. Antibodies were prepared in accordance with conventional methods, where the chemically synthesized peptide is used as an immunogen conjugated to known immunogenic carriers, such keyhole limpet hemocyanin ("KLH"), the surface antigen of the hepatitis-B-virus ("HBsAg"), other viral or eukaryotic proteins, or the like. Various adjuvants may be employed, with a series of injections, as appropriate. For monoclonal antibodies, after one or more booster injections, the spleen can isolated, the lymphocytes immortalized by cell fusion, and then screened for high affinity antibody binding. The immortalized cells, (hybridoma), producing the desired antibodies may then be expanded. For a more detailed description, see Monoclonal Antibodies: A Laboratory Manual, Harlow and Lane eds., Cold Spring Harbor Laboratories, Cold Spring Harbor, N.Y., 1988, hereby incorporated by reference.

Isolation of Native Phoenixin Peptides

Homogenates were prepared from heart tissues of adult rats. The supernatant of the rat heart homogenates were passed through C18 column extraction cartridges and P6 gel filtration to further purify native peptide candidates. The immunoreactive fractions as determined by conventional enzyme immunoassay ("EIA") in which labeled chemically synthesized peptides as described above compete with unlabeled native phoenixin peptide for a limited quantity of the anti-phoenixin peptide antibodies, produced as above described. The label can be biotin complex which by reaction with streptavidin horseradish peroxidase and sequent reaction of the horseradish peroxidase with colormetric or fluorescence substrates can be quantitated. Immuno-reactive fractions were further purified either by P6 size fractionation gel (Bio-Rad laboratory, Hercules, Calif.) or by ion exchange by application to carboxylmethyl cellulose ("CMC") resin and elution with 0.2 M ammonium acetate. Since the P6 size fractionation gave the best immunoreactive results, this immunoreactive fractions were then further purified by a first RP-HPLC separation as above described and the resulting immunoreactive fractions further purified by a subsequent second RP-HPLC separation, as above described.

Now referring primarily to FIG. 61, a first RP-HPLC separation plot shows the elution of peptides (peaks above the baseline) resulting from application of RP-HPLC to the immunoreactive fractions obtained by the above described ion exchange procedure. The eluted fractions containing peptides were assayed by the EIA procedure above described and the level of immunoreactivity superimposed over the first RP-HPLC plot showing that the eluted fractions corresponding with the peaks occurring at about 26.5 minutes and about 27 minutes respectively contain native phoenixin peptides which bind the corresponding anti-peptide antibodies produced as above described.

Now referring primarily to FIG. 62, which shows the mass spectrum resulting from mass spectroscopy of the fraction containing the peptides eluting at about 26.5 minutes in the first RP-HPLC separation. The mass spectrum achieved by matrix-assisted laser desorption/ionization time of flight ("MALDI-TOF") shows that the fraction corresponding to the peak eluted at about 26.5 minutes contains native phoenixin peptides DVQPPGLKVWSDPF-NH2 (SEQ. ID NO: 9), QPPGLKVWSDPF-NH2 (SEQ. ID NO: 11) and AGIVQEDVQPPGLKVWSDPF-NH2 (SEQ. ID NO: 7).

Now referring primarily to FIG. 63, which shows the mass spectrum resulting from mass spectroscopy of the fraction containing the peak eluting at about 27 minutes in the first RP-HPLC separation. The mass spectrum by high voltage power in MALDI-TOF shows that the fraction containing the peak eluting at about 27 minutes contains several native phoenixin peptides, QPPGLKVWSDPFG (SEQ. ID NO: 5), VQPPGLKVWSDPF-NH2 (SEQ. ID NO: 8) DVQPPGLKVWSDPF-NH2 (SEQ. ID NO: 9), DVQPPGLKVWSDPFG (SEQ. ID NO: 3) and AGIVQEDVQPPGLKVWSDPF-NH2 (SEQ. ID NO: 7).

Now referring primarily to FIG. 64, which shows a second RP-HPLC separation plot evidencing the elution of peptides (peaks above the baseline) resulting from application of RP-HPLC to the immunoreactive fractions obtained by the above described first RP-HPLC separation. The eluted fractions containing peptides were assayed by the EIA procedure above described and the level of immunoreactivity superimposed over the first RP-HPLC plot showing that the eluted fractions corresponding with the peak occurring at about 26 to 26.5 minutes contain native phoenixin peptides which bind the corresponding anti-peptide antibodies, as above described.

Now referring primarily to FIG. 65, which shows the mass spectrum resulting from mass spectroscopy of the fraction eluting at about 26 to 26.5 minutes in the second RP-HPLC separation. The mass spectrum shows that the eluted fraction corresponding to the peak at about 26 to 26.5 minutes contains native phoenixin peptides DVQPPGLKVWSDPFG (SEQ. ID NO: 3) and DVQPPGLKVWSDPF-NH2 (SEQ. ID NO: 9).

Detection of Phoenixin Peptide in Tissue Sections

Now referring primarily to FIGS. 66A through 66D each of which show tissue sections of rat medulla on glass slides fixed and immunostained by conventional immunohistochemical staining procedures using the anti-phoenixin antibodies raised against AGIVQEDVQPPGLKVWSDPF-NH2 (SEQ. ID NO: 7) and DVQPPGLKVWSDPF-NH2 (SEQ. ID NO: 9). Phoenixin-immunofluorescent cell processes are noted in the spinal trigeminal tract (Sp5) and vagal afferents in FIG. 66A; an enlarged area of spinal trigeminal tract and vagal afferents in 66B; immunofluorescent cell processes in the medial nucleus of solitary tract (SolM) and central nucleus of solitary tract (SolC) in FIG. 66C; immunofluorescent cell processes projecting from the spinal trigeminal tract to the nucleus of ambiguus (nAmb) in FIG. 66D. Scale bar: A, 250 µm; B, C and D, 100 µm.

Generally, immunohistochemical staining on frozen tissue sections includes establishing the tissue sections on glass slides. Fixing the tissue sections with a suitable fixative such as pre-cooled acetone (−20° C.) for 10 min. The fixative can be poured off and the residue acetone evaporated. The slides can be rinsed with a buffer such as 10 mM phosphate buffered saline (PBS) at a neutral pH for 2 changes, 5 min each. The slides can be incubated in about 0.3% H2O2 solution in PBS at room temperature for 10 minutes to block endogenous peroxidase activity. The slides are subsequently rinsed in 300 ml PBS for 2 changes, 5 min each. An optional blocking buffer can be used including for example 10% normal goat serum in PBS onto the tissue sections and incubated at room temperature for 1 hour. Apply diluted primary antibody raised against SEQ. ID NO: 7 and SEQ. ID NO: 9 in antibody dilution buffer, of 0.5% bovine serum albumin in PBS to the sections on the slides and incubate for 1 hour at room temperature or overnight at 4° C. Rinse the slides in about 300 ml PBS for 2 changes, 5 min each. Apply 100 µl an appropriately diluted biotinylated secondary antibody in the antibody dilution buffer to tissue sections on the slides and incubate at room temperature for about 30 min. Rinse the slides in 300 ml PBS for 2 changes, 5 min each. Add 100 µl pre-diluted horse radish conjugates using the antibody dilution buffer to the sections on the slides and incubate in a humidified chamber at room temperature for 30 min protected from light. Rinse the slides in about 300 ml PBS for 2 changes, 5 min each. Apply about 100 µl 3,3'-diaminobenzidine ("DAB") substrate solution freshly made just before use: 0.05% DAB-0.015% H2O2 in PBS to the sections on the slides to reveal the color of the antibody staining. Allow the color development for <5 min until the desired color intensity is reached. Wash slides in 300 ml PBS for 2 changes 5 min each. Optionally, counter stain slides by immersing sides in hematoxylin for 1-2 min. Rinse the slides in running tap water for >15 min. Dehydrate the tissue slides through 4 changes of alcohol (95%, 95%, 100% and 100%), 5 min each. Clear the tissue slides in 3 changes of xylene and coverslip using mounting solution. Observe the color of the antibody staining in the tissue sections under microscopy.

Now referring to FIGS. 67A through 67D, the immunoactivity of native Phoenixin peptides in tissue samples of the rat forebrain prepared as above-described is shown. Phoenixin-immunoreactive cell bodies are detected in the caudate putamen (CPu) in FIG. 67A; fine cell processes can also be seen in the CPu in FIG. 67B; amygdala in FIG. 67C, and periventricular nucleus (Pe) in FIG. 67 D. Scale bar: A, 100 µm; B, C and D, 50 µm.

Now referring to FIGS. 68A through 68F, the immunoactivity of native phoenixin peptides in tissue sections of rat spinal cord prepared as above-described is shown. Phoenixin-immunofluorescence occurs in the superficial dorsal horn of cervical (FIGS. 68A and 68B), thoracic (FIGS. 68C and 68D), and lumbar (FIG. 68E) segments. FIG. 68F shows a lumbar section processed with phoenixin-antiserum preabsorbed with the peptide (1 µg/ml overnight; immunofluorescence is not detected in the dorsal horn. Scale bar: A, C, E and F, 250 µm; B and D, 100 µm.

Detection of Phoenixin Peptides in Tissue Homogenate Extracts and Blood Plasma

Now referring primarily to FIG. 69, which shows a bar graph that plots the tissue distribution and concentration of native phoenixin peptides corresponding to AGIVQEDVDVQPPGLKVWSDPF-NH2 (SEQ. ID NO: 7) and DVQPPGLKVWSDPF-NH2 (SEQ. ID NO: 9). Homogenates of porcine or bovine or rat tissue of heart, lung, kidney, spinal cord, small intestine, liver, pancreas, hypothalamus, spleen, and thymus were prepared as above-described and the resulting fractions were processed by the above-described peptides extraction procedure and were assayed by radioimmunoassay ("RIA") or Enzyme Immunoassay (EIA) using antibodies raised to AGIVQEDVQPPGLKVWSDPF-NH2 (SEQ. ID NO: 7). The antibodies raised to AGIVQEDVQPPGLKVWSDPF-NH2 (SEQ. ID NO: 7) were also shown to be 100% cross-reactive with DVQPPGLKVWSDPF-NH2 (SEQ. ID NO: 9) but less than 0.5% cross-reactive to DVQPPGLKVWSDPFG (SEQ. ID NO: 3). The intra-assay variability was about 5% with a detection limit of about 34 picograms/milliliter ("pg/mL") and an EC50 of about 200 pg/ML. Protein concentrations were determined by bicinchoninic acid ("BCA") protein assay in accordance to the protocol of the manufacturer Thermo Scientific, Rockford, Ill. using bovine serum albumin ("BSA") as a standard. Data are expressed as the mean±SEM of the results from three duplicate assays in immunoreactive phoenixin peptide per milligram of protein.

As shown in FIG. 69 and Table 1 below, tissues of the liver, pancreas, spleen, kidney and thymus produce substantially less immuno-reactive phoenixin peptides than the tissues of the heart and hypothalamus. Using the Fluorescence Phoenixin Enzyme-immunoassay, the phoenixin peptide level in human blood plasma without C18 extraction has been determined to be about 35.5±1.72 pg/ml.

TABLE 1

Tissue Level of Phoenixins Detected by Fluorescent Phoenixin Enzyme-Immunoassay

| Tissue Homogenates (species) | Concentration (pg/mg tissue protein) |
| --- | --- |
| Cerebrum (rat) | Not Detected |
| Cerebellum (rat) | 0.051 ± 0.002 |
| Hypothalamus (rat) | 363.292 ± 0.384 |
| Hippocampus (rat) | Not Detected |
| Pons (rat) | 0.218 ± 0.006 |
| Pituitary (rat) | 12628.782 ± 505.026 |
| Heart (rat) | 1360.539 ± 115.917 |
| Lung (rat) | 1924.667 ± 153.15 |
| Stomach (porcine) | 520.446 ± 119.702 |
| Small Intestine (rat) | 122302.492 ± 18315.776 |
| Kidney (rat) | 8530.822 ± 1207.631 |
| Spleen (rat) | 5.393 ± 0.067 |
| Pancreas (rat) | 29.128 ± 0.434 |
| Liver (rat) | 585.518 ± 48.389 |
| Ovary (rat) | 12.992 ± 0.009 |
| Liver (porcine) | 0.0887 ± 0.005 |

Effects of Phoenixin Peptides on Pituitary Cells

Now referring primarily to FIG. 70, a bar graph compares the production of cAMP in rat pituitary cells challenged with AGIVQEDVQPPGLKVWSDPF-NH2 (SEQ. ID NO: 7) as shown in FIG. 7, DVQPPGLKVWSDPFG (SEQ. ID NO: 3) as shown in FIG. 3, DVQPPGLKVWSDPF-NH2 (SEQ. ID NO: 9) as shown in FIG. 9 and a PBS control.

Rat pituitary adenoma cells, RC-4B/C (CRL-1903; ATCC, Manassas, Va., USA), were cultured in Dulbecco's Modified Eagle's Medium and Minimum Essential Alpha Medium (Invitrogen, CA, USA) supplemented with 0.01 mM non-essential amino acids, 15 mM HEPES, 2.5 ng/ml epidermal growth factor, and dialyzed, heat-inactivated fetal bovine serum ("FBS") at 37° C. in a humidified cell incubator containing 5% carbon dioxide ("CO2"). After 2 days of cell cultured in 24 wells plate, cell were equilibrated for 2 hours in serum-free medium and then incubated with 0.1 mM 3-isobutyl-1-methylxanthine ("IBMX") in serum-free medium 30 min again. Then, cells were challenged with either 100 nM of AGIVQEDVQPPGLKVWSDPF-NH2 (SEQ. ID NO: 7), DVQPPGLKVWSDPFG (SEQ. ID NO: 3), DVQPPGLKVWSDPF-NH2 (SEQ. ID NO: 9), or a PBS-control in the presence of IBMX and incubated for 30 min. After incubation, supernatant medium was then aspirated and the cells in each well were extracted by 70% cold ethanol. Alcohol was evaporated in a vacuum concentrator (PN: AES 2000, Savant, Hicksvile, N.Y., USA) Thereafter, cAMP content was determined by using a cAMP Biotrak enzyme immunoassay kit (GE healthcare-Amersham, Piscataway, N.J., USA) in accordance with the protocol of the manufacturer.

Also, rat pituitary adenoma cells, RC-4B/C cells, were used in the assay of radioligand binding. For the binding displacement, cells were incubated for 30 min with 50 pM 125I-Y0-Phoenixin-20 (amide SEQ. ID NO: 7) in the absence or presence of increasing concentrations of un-labeled Phoenixin-20 amide (amide SEQ. ID NO: 7) or phoenixin-14 amide (amide SEQ. ID NO: 9). Nonspecific binding was defined as total binding in the presence of 1 µM unlabeled Phoenixin-20 amide (amide SEQ. ID NO: 7) or phoenixin-14 amide (amide SEQ. ID NO: 9). After termination of the binding reaction by washing the cells with 1 ml of cold PBS, cells were solubilized with 0.5 ml of 1% SDS, and radioactivity was detected in a gamma counter. From non-linear curve fitting, the IC50 for Phoenixin-20 amide is 21.5 nM and for Phoenixin-14 amide is 17.9 nM.

As indicated in FIG. 70, AGIVQEDVQPPGLKVWSDPF-NH2 (SEQ. ID NO: 7), DVQPPGLKVWSDPFG (SEQ. ID NO: 3), DVQPPGLKVWSDPF-NH2 (SEQ. ID NO: 9) can increase the intracellular cAMP production in rat pituitary adenoma cells greater than two fold and even three-fold over the PBS control. Data are expressed as a percentage of the control value (PBS-control, 100%; 4.94±0.5 pmol/mg protein).

Uses of Phoenixin Peptides

Phoenixin peptides SEQ. ID NOS: 2 through 60 can be utilized in four general areas. Firstly, as antigens in the form of one or more Phoenixin peptides SEQ. ID NOS: 2 through 60 which can be utilized in the assays above or below described or to raise monoclonal or polyclonal antibodies, as above described, The resulting monoclonal or polyclonal antibodies can be useful in binding one or more of the phoenixin propeptide, phoenixin peptides, or the like.

Secondly, as molecular tools or reagents in kits including one or more chemically synthesized phoenixin peptides SEQ. ID NOS: 2 through 60 which can be accompanied by antibodies raised to one or more of the phoenixin peptides.

The kits can be useful for example in radio-immunoassays ("RIA"), enzyme-linked immunosorbent assay ("ELISA"), or enzyme immunoassay ("EIA"), or the like, of tissue or cell homogenates or eluted fractions resulting from purification protocols using gel filtration, ion exchange chromatography, reverse phase chromatography, immunoprecipitation or the like, and for the immunohistochemical analysis of tissues, or as standards for chromatography or mass spectroscopy, or as a biomarker in the disease screening.

Thirdly, as a diagnostic tool in clinical usage for assessment of certain diseases. Since native phoenixin peptides can be functional peptides in human or animal physiology, the absence or abnormal levels (whether abnormally high or low compared to normal values) of phoenixin peptides can correlate with other physiological factors or symptoms which indicate specific diseases. The presence of a certain amount of Phoenixin peptide in the blood or tissues can be used as an indication or as a guide index for certain medical treatments.

Fourthly, the phoenixin peptides can play a functional role in normal physiology. Over-expression or under-expression of native phoenixin peptides can result in the related disease or dysfunction. Therefore, administration of one or more phoenixin peptide(s) or phoenixin peptides to the animal or human body, or contact with cells that bind, competitively bind, transfer, or otherwise utilize phoenixin peptides to regulate or modulate a physiological pathway can reverse or correct the disease state. In order to maximize therapeutic effectiveness, administration of one or more phoenixin peptides may be accomplished through different methods such as intravenous, intramuscular, sub-cutaneous, or the like, alone or in conjunction with other pharmaceutical reagents in amounts sufficient to generate a therapeutic effect, such as cardiovasular response to lower blood pressure, empty the bowel, release gonadotropins, or the like. As but one example, one or more of phoenixin SEQ. ID NOS: 2 to 60 can be administered to animals to achieve a decrease in blood pressure. Additionally, one or more Phoenixin peptides SEQ. ID NOS: 2 to 60 can be administered to animals to regulate cell signal and in particular phoenixin peptides AGIVQEDVQPPGLKVWSDPF (SEQ. ID NO: 2), DVQPPGLKVWSDPFG (SEQ. ID NO: 3), DVQPPGLKVWSDPF (SEQ. ID NO: 4), QPPGLKVWSDPFG (SEQ. ID NO: 5) VQPPGLKVWSDPF (SEQ. ID NO: 6), AGIVQEDVQPPGLKVWSDPF-NH2 (SEQ. ID NO: 7), VQPPGLKVWSDPF-NH2 (SEQ. ID NO: 8), DVQPPGLKVWSDPF-NH2 (SEQ. ID NO: 9), DVQPPGLKVdWSDPF-NH2 (SEQ. ID NO: 31), DVQPPGLKVWSDdPF-NH2 (SEQ. ID NO: 32) and DVQPPGLKVdWSDPW-NH2 (SEQ. ID NO: 60) can be utilized to modulate cAMP production in cells.

Now referring to FIG. 71, the alignment of the region of phoenixin (1-20), phoenixin (7-20), and phoenixin (7-21) is shown in different species of animals. The sequence alignment evidences that the sequence of phoenixin (1-20) in the prepro-proteins is identical between the species of human, bovine, rat, and mouse. phoenixin (1-20) in the species of canis and pig have one residue difference which is one substitution of valine or isoleucine for the residue of isoleucine or valine. Accordingly, the sequences, synthesis or isolation of phoenixin peptides, analysis, and function as above described can be conserved between species.

Now referring to the Figures in general and the description of the Figures above, any reference to human phoenixin or human phoenixin peptides along with the residue position identifiers in the propeptide human phoenixin (Swiss-Prot: Q8N5G0) are for alignment reference only and it is not intended that these references admit or suggest that any of the phoenixin peptides shown in the Figures or described above were identified in the prior art, occur in nature, or structure or function of propeptide human phoenixin is similar to the described phoenixin peptides.

As can be easily understood from the foregoing, the basic concepts of the present invention may be embodied in a variety of ways. The invention including the best mode involves numerous and varied embodiments of phoenixin/phoenixin peptides useful for the production of antibodies, diagnostic screening and assays, modulation of cellular cAMP, and treatment of disorders benefited by peptides which can modulate cAMP, hypertension, and smooth muscle response.

As such, the particular embodiments or elements of the invention disclosed by the description including the best mode or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "a chemically synthesized peptide" should be understood to encompass disclosure of the act of "chemically synthesizing a peptide"—whether explicitly discussed or not—and, conversely, were there effectively disclosure of the act of "chemically synthesizing a peptide", such a disclosure should be understood to encompass disclosure of "a chemically synthesized peptide" and even a "means for chemically synthesizing a peptide." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "a light source" refers to one or more of those light sources. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

Thus, the applicant(s) should be understood to claim at least: i) each of the phoenixin peptides herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A purified and isolated polypeptide comprising the amino acid sequence selected from the group consisting of SEQ ID NOs: 7 through 60, or a variant thereof having at least 90% sequence identity with any one of SEQ ID NOs: 7 through 53, 57, 59 and 60.

2. The purified and isolated polypeptide according to claim 1, wherein said purified and isolated polypeptide comprises the amino acid sequence having at least 90% to 95% sequence identity with any one of SEQ ID NOs: 7 through 53, 57, 59 and 60.

3. The purified and isolated polypeptide according to claim 1, wherein said purified and isolated polypeptide comprises the amino acid sequence having at least 95% to 99% sequence identity with any one of SEQ ID NOs: 7 through 53, 57, 59 and 60.

4. A kit for detection of a peptide or propeptide Swiss-Prot: Q8N5G0, comprising one or more purified and isolated polypeptides comprising the amino acid sequence selected from the group consisting of SEQ ID NOs: 7 through 60, or a variant thereof having at least 90% sequence identity with any one of SEQ ID NOS: 7 through 53, 57, 59 and 60.

5. The kit according to claim 4, wherein said purified and isolated polypeptide comprises the amino acid sequence having at least 90% to 95% sequence identity with any one of SEQ ID NOs: 7 through 53, 57, 59, and 60.

6. The kit according to claim 4, wherein said purified and isolated polypeptide comprises the amino acid sequence having at least 95% to 99% sequence identity with any one of SEQ ID NOs: 7 through 53, 57, 59 and 60.

7. A kit for detection of a peptide or propeptide Swiss-Prot: Q8N5G0, comprising one or more purified and isolated polypeptides consisting of the amino acid sequence selected from the group consisting of SEQ ID NOs: 7 through 60.

* * * * *

SEQUENCE LISTING

```
<160> NUMBER OF SEQ ID NOS: 66

<210> SEQ ID NO 1
<211> LENGTH: 168
<212> TYPE: PRT
<213> ORGANISM: Homo sapiens

<400> SEQUENCE: 1

Met Val Lys Glu Val Trp Arg Val Leu Arg Glu Glu Pro Gly Arg Arg
1               5                   10                  15

Lys Glu Ser Arg Gln Asn Arg Ala Arg Gly Asn Arg Val Gln Gln Asn
            20                  25                  30

Ser Ser Asn Leu Asn Pro Thr Pro Ala Pro Gly Pro His Ser Thr Glu
        35                  40                  45

Ser Arg Gly Arg Arg Ala Gly Ser Glu Ala Pro Pro Arg Pro Gly
    50                  55                  60

Ser Glu Ser Leu Ser Thr Ser Ser Glu Arg Gly His Gly Pro Ala Val
65                  70                  75                  80

Gly Asn Leu Val Ser Glu Ser Ala Gly Arg Ser Ala Gly Gln Gly Ser
                85                  90                  95

Pro Gly Pro Asp Ala Met Ser Arg Asn Leu Arg Thr Ala Leu Ile Phe
            100                 105                 110

Gly Gly Phe Ile Ser Leu Ile Gly Ala Ala Phe Tyr Pro Ile Tyr Phe
        115                 120                 125

Arg Pro Leu Met Arg Leu Glu Glu Tyr Lys Lys Glu Gln Ala Ile Asn
    130                 135                 140

Arg Ala Gly Ile Val Gln Glu Asp Val Gln Pro Pro Gly Leu Lys Val
145                 150                 155                 160
```

```
Trp Ser Asp Pro Phe Gly Arg Lys
            165

<210> SEQ ID NO 2
<211> LENGTH: 20
<212> TYPE: PRT
<213> ORGANISM: Homo sapiens

<400> SEQUENCE: 2

Ala Gly Ile Val Gln Glu Asp Val Gln Pro Pro Gly Leu Lys Val Trp
1               5                   10                  15

Ser Asp Pro Phe
            20

<210> SEQ ID NO 3
<211> LENGTH: 15
<212> TYPE: PRT
<213> ORGANISM: Homo sapiens

<400> SEQUENCE: 3

Asp Val Gln Pro Pro Gly Leu Lys Val Trp Ser Asp Pro Phe Gly
1               5                   10                  15

<210> SEQ ID NO 4
<211> LENGTH: 14
<212> TYPE: PRT
<213> ORGANISM: Homo sapiens

<400> SEQUENCE: 4

Asp Val Gln Pro Pro Gly Leu Lys Val Trp Ser Asp Pro Phe
1               5                   10

<210> SEQ ID NO 5
<211> LENGTH: 13
<212> TYPE: PRT
<213> ORGANISM: Homo sapiens

<400> SEQUENCE: 5

Gln Pro Pro Gly Leu Lys Val Trp Ser Asp Pro Phe Gly
1               5                   10

<210> SEQ ID NO 6
<211> LENGTH: 13
<212> TYPE: PRT
<213> ORGANISM: Homo sapiens

<400> SEQUENCE: 6

Val Gln Pro Pro Gly Leu Lys Val Trp Ser Asp Pro Phe
1               5                   10

<210> SEQ ID NO 7
<211> LENGTH: 20
<212> TYPE: PRT
<213> ORGANISM: Homo sapiens
<220> FEATURE:
<221> NAME/KEY: MISC_FEATURE
<222> LOCATION: (20)..(20)
<223> OTHER INFORMATION: C-terminal amidation

<400> SEQUENCE: 7

Ala Gly Ile Val Gln Glu Asp Val Gln Pro Pro Gly Leu Lys Val Trp
1               5                   10                  15

Ser Asp Pro Phe
            20
```

```
<210> SEQ ID NO 8
<211> LENGTH: 13
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: C-terminal amidation

<400> SEQUENCE: 8

Val Gln Pro Pro Gly Leu Lys Val Trp Ser Asp Pro Phe
1               5                   10

<210> SEQ ID NO 9
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: C-terminal amidation

<400> SEQUENCE: 9

Asp Val Gln Pro Pro Gly Leu Lys Val Trp Ser Asp Pro Phe
1               5                   10

<210> SEQ ID NO 10
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (16)..(16)
<223> OTHER INFORMATION: C-terminal amidation

<400> SEQUENCE: 10

Xaa Glu Asp Val Gln Pro Pro Gly Leu Lys Val Trp Ser Asp Pro Phe
1               5                   10                  15

<210> SEQ ID NO 11
<211> LENGTH: 12
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: C-terminal amidation

<400> SEQUENCE: 11

Gln Pro Pro Gly Leu Lys Val Trp Ser Asp Pro Phe
1               5                   10

<210> SEQ ID NO 12
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (12)..(12)
<223> OTHER INFORMATION: C-terminal amidation
```

```
<400> SEQUENCE: 12

Xaa Pro Pro Gly Leu Lys Val Trp Ser Asp Pro Phe
1               5                   10

<210> SEQ ID NO 13
<211> LENGTH: 20
<212> TYPE: PRT
<213> ORGANISM: Homo sapiens
<220> FEATURE:
<221> NAME/KEY: MISC_FEATURE
<222> LOCATION: (20)..(20)
<223> OTHER INFORMATION: C-terminal methylamidation

<400> SEQUENCE: 13

Ala Gly Ile Val Gln Glu Asp Val Gln Pro Pro Gly Leu Lys Val Trp
1               5                   10                  15

Ser Asp Pro Phe
            20

<210> SEQ ID NO 14
<211> LENGTH: 13
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: C-terminal methylamidation

<400> SEQUENCE: 14

Val Gln Pro Pro Gly Leu Lys Val Trp Ser Asp Pro Phe
1               5                   10

<210> SEQ ID NO 15
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: C-terminal methylamide
<220> FEATURE:
<221> NAME/KEY: MISC_FEATURE
<222> LOCATION: (14)..(14)
<223> OTHER INFORMATION: C-terminal methylamidation

<400> SEQUENCE: 15

Asp Val Gln Pro Pro Gly Leu Lys Val Trp Ser Asp Pro Phe
1               5                   10

<210> SEQ ID NO 16
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (16)..(16)
<223> OTHER INFORMATION: C-terminal methylamidation

<400> SEQUENCE: 16

Xaa Glu Asp Val Gln Pro Pro Gly Leu Lys Val Trp Ser Asp Pro Phe
1               5                   10                  15

<210> SEQ ID NO 17
<211> LENGTH: 12
```

```
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: C-terminal methyl amidation

<400> SEQUENCE: 17

Gln Pro Pro Gly Leu Lys Val Trp Ser Asp Pro Phe
1               5                   10

<210> SEQ ID NO 18
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (12)..(12)
<223> OTHER INFORMATION: C-terminal methylamidation

<400> SEQUENCE: 18

Xaa Pro Pro Gly Leu Lys Val Trp Ser Asp Pro Phe
1               5                   10

<210> SEQ ID NO 19
<211> LENGTH: 20
<212> TYPE: PRT
<213> ORGANISM: Homo sapiens
<220> FEATURE:
<221> NAME/KEY: MISC_FEATURE
<222> LOCATION: (20)..(20)
<223> OTHER INFORMATION: C-terminal ethylamidation

<400> SEQUENCE: 19

Ala Gly Ile Val Gln Glu Asp Val Gln Pro Pro Gly Leu Lys Val Trp
1               5                   10                  15

Ser Asp Pro Phe
            20

<210> SEQ ID NO 20
<211> LENGTH: 13
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: C-terminal ethylamidation

<400> SEQUENCE: 20

Val Gln Pro Pro Gly Leu Lys Val Trp Ser Asp Pro Phe
1               5                   10

<210> SEQ ID NO 21
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: C-terminal ethylamidation

<400> SEQUENCE: 21

Asp Val Gln Pro Pro Gly Leu Lys Val Trp Ser Asp Pro Phe
1               5                   10
```

```
<210> SEQ ID NO 22
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (16)..(16)
<223> OTHER INFORMATION: C-terminal ethylamidation

<400> SEQUENCE: 22

Xaa Glu Asp Val Gln Pro Pro Gly Leu Lys Val Trp Ser Asp Pro Phe
1               5                   10                  15

<210> SEQ ID NO 23
<211> LENGTH: 12
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: C-terminal ethylamidation

<400> SEQUENCE: 23

Gln Pro Pro Gly Leu Lys Val Trp Ser Asp Pro Phe
1               5                   10

<210> SEQ ID NO 24
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (12)..(12)
<223> OTHER INFORMATION: C-terminal ethylamidamidation

<400> SEQUENCE: 24

Xaa Pro Pro Gly Leu Lys Val Trp Ser Asp Pro Phe
1               5                   10

<210> SEQ ID NO 25
<211> LENGTH: 14
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: valine at position 2 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 25

Asp Val Gln Pro Pro Gly Leu Lys Val Trp Ser Asp Pro Phe
1               5                   10

<210> SEQ ID NO 26
<211> LENGTH: 14
<212> TYPE: PRT
<213> ORGANISM: Homo sapiens
<220> FEATURE:
<221> NAME/KEY: MISC_FEATURE
```

```
<222> LOCATION: (4)..(4)
<223> OTHER INFORMATION: proline at position 4 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 26

Asp Val Gln Pro Pro Gly Leu Lys Val Trp Ser Asp Pro Phe
1               5                   10

<210> SEQ ID NO 27
<211> LENGTH: 14
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: proline at position 5 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 27

Asp Val Gln Pro Pro Gly Leu Lys Val Trp Ser Asp Pro Phe
1               5                   10

<210> SEQ ID NO 28
<211> LENGTH: 14
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: alanine at position 6 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 28

Asp Val Gln Pro Pro Ala Leu Lys Val Trp Ser Asp Pro Phe
1               5                   10

<210> SEQ ID NO 29
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: leucine at position 7 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 29

Asp Val Gln Pro Pro Gly Leu Lys Val Trp Ser Asp Pro Phe
1               5                   10

<210> SEQ ID NO 30
<211> LENGTH: 14
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: valine at position 9 is the D isoform
<220> FEATURE:
```

```
<221> NAME/KEY: MISC_FEATURE
<222> LOCATION: (14)..(14)
<223> OTHER INFORMATION: C-terminal amidation

<400> SEQUENCE: 30

Asp Val Gln Pro Pro Gly Leu Lys Val Trp Ser Asp Pro Phe
1               5                   10

<210> SEQ ID NO 31
<211> LENGTH: 14
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: tryptophan at position 10 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 31

Asp Val Gln Pro Pro Gly Leu Lys Val Trp Ser Asp Pro Phe
1               5                   10

<210> SEQ ID NO 32
<211> LENGTH: 14
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: proline at position 13 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 32

Asp Val Gln Pro Pro Gly Leu Lys Val Trp Ser Asp Pro Phe
1               5                   10

<210> SEQ ID NO 33
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: phenylalanine at position 14 is the D isoform
<220> FEATURE:
<221> NAME/KEY: MISC_FEATURE
<222> LOCATION: (14)..(14)
<223> OTHER INFORMATION: C-terminal amidation

<400> SEQUENCE: 33

Asp Val Gln Pro Pro Gly Leu Lys Val Trp Ser Asp Pro Phe
1               5                   10

<210> SEQ ID NO 34
<211> LENGTH: 14
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: X at position 14 is the D isoform of 1, 2, 3,
      4, -tetrahydroisoquinoline-3-carboxylic acid
<220> FEATURE:
<221> NAME/KEY: MISC_FEATURE
<222> LOCATION: (14)..(14)
```

```
<223> OTHER INFORMATION: C-terminal amidation

<400> SEQUENCE: 34

Asp Val Gln Pro Pro Gly Leu Lys Val Trp Ser Asp Pro Xaa
1               5                   10

<210> SEQ ID NO 35
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: alanine at position 1 is the D isoform
<220> FEATURE:
<221> NAME/KEY: MISC_FEATURE
<222> LOCATION: (20)..(20)
<223> OTHER INFORMATION: C-terminal amidation

<400> SEQUENCE: 35

Ala Gly Ile Val Gln Glu Asp Val Gln Pro Pro Gly Leu Lys Val Trp
1               5                   10                  15

Ser Asp Pro Phe
            20

<210> SEQ ID NO 36
<211> LENGTH: 20
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: alanine at position 2 is the D isoform
<220> FEATURE:
<221> NAME/KEY: MISC_FEATURE
<222> LOCATION: (20)..(20)
<223> OTHER INFORMATION: C-terminal amidation

<400> SEQUENCE: 36

Ala Ala Ile Val Gln Glu Asp Val Gln Pro Pro Gly Leu Lys Val Trp
1               5                   10                  15

Ser Asp Pro Phe
            20

<210> SEQ ID NO 37
<211> LENGTH: 20
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: valine at position 4 is the D isoform
<220> FEATURE:
<221> NAME/KEY: MISC_FEATURE
<222> LOCATION: (20)..(20)
<223> OTHER INFORMATION: C-terminal amidation

<400> SEQUENCE: 37

Ala Gly Ile Val Gln Glu Asp Val Gln Pro Pro Gly Leu Lys Val Trp
1               5                   10                  15

Ser Asp Pro Phe
            20

<210> SEQ ID NO 38
<211> LENGTH: 20
<212> TYPE: PRT
<213> ORGANISM: Homo sapiens
<220> FEATURE:
```

```
<221> NAME/KEY: MISC_FEATURE
<222> LOCATION: (8)..(8)
<223> OTHER INFORMATION: valine at position 8 is the D isoform
<220> FEATURE:
<221> NAME/KEY: MISC_FEATURE
<222> LOCATION: (20)..(20)
<223> OTHER INFORMATION: C-terminal amidation

<400> SEQUENCE: 38

Ala Gly Ile Val Gln Glu Asp Val Gln Pro Pro Gly Leu Lys Val Trp
1               5                   10                  15

Ser Asp Pro Phe
            20

<210> SEQ ID NO 39
<211> LENGTH: 20
<212> TYPE: PRT
<213> ORGANISM: Homo sapiens
<220> FEATURE:
<221> NAME/KEY: MISC_FEATURE
<222> LOCATION: (17)..(17)
<223> OTHER INFORMATION: serine at position 17 is the D isoform
<220> FEATURE:
<221> NAME/KEY: MISC_FEATURE
<222> LOCATION: (20)..(20)
<223> OTHER INFORMATION: C-terminal amidation

<400> SEQUENCE: 39

Ala Gly Ile Val Gln Glu Asp Val Gln Pro Pro Gly Leu Lys Val Trp
1               5                   10                  15

Ser Asp Pro Phe
            20

<210> SEQ ID NO 40
<211> LENGTH: 20
<212> TYPE: PRT
<213> ORGANISM: Homo sapiens
<220> FEATURE:
<221> NAME/KEY: MISC_FEATURE
<222> LOCATION: (19)..(19)
<223> OTHER INFORMATION: proline at position 19 is the D isoform
<220> FEATURE:
<221> NAME/KEY: MISC_FEATURE
<222> LOCATION: (20)..(20)
<223> OTHER INFORMATION: C-terminal amidation

<400> SEQUENCE: 40

Ala Gly Ile Val Gln Glu Asp Val Gln Pro Pro Gly Leu Lys Val Trp
1               5                   10                  15

Ser Asp Pro Phe
            20

<210> SEQ ID NO 41
<211> LENGTH: 20
<212> TYPE: PRT
<213> ORGANISM: Homo sapiens
<220> FEATURE:
<221> NAME/KEY: MISC_FEATURE
<222> LOCATION: (20)..(20)
<223> OTHER INFORMATION: phenylalanine at position 20 is the D isoform
<220> FEATURE:
<221> NAME/KEY: MISC_FEATURE
<222> LOCATION: (20)..(20)
<223> OTHER INFORMATION: C-terminal amidation

<400> SEQUENCE: 41

Ala Gly Ile Val Gln Glu Asp Val Gln Pro Pro Gly Leu Lys Val Trp
1               5                   10                  15
```

Ser Asp Pro Phe
            20

<210> SEQ ID NO 42
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (20)..(20)
<223> OTHER INFORMATION: C-terminal amidation

<400> SEQUENCE: 42

Ala Gly Ile Val Gln Glu Asp Val Gln Pro Pro Gly Leu Lys Val Trp
1               5                   10                  15

Ser Asp Pro Phe
            20

<210> SEQ ID NO 43
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (13)..(13)
<223> OTHER INFORMATION: C-terminal amidation

<400> SEQUENCE: 43

Val Gln Pro Pro Gly Leu Lys Val Trp Ser Asp Pro Phe
1               5                   10

<210> SEQ ID NO 44
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (14)..(14)
<223> OTHER INFORMATION: C-terminal amidation

<400> SEQUENCE: 44

Asp Val Gln Pro Pro Gly Leu Lys Val Trp Ser Asp Pro Phe
1               5                   10

<210> SEQ ID NO 45
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal formylation
<220> FEATURE:
<221> NAME/KEY: MISC_FEATURE
<222> LOCATION: (20)..(20)
<223> OTHER INFORMATION: C-terminal amidation

<400> SEQUENCE: 45

Ala Gly Ile Val Gln Glu Asp Val Gln Pro Pro Gly Leu Lys Val Trp
1               5                   10                  15

Ser Asp Pro Phe
            20

<210> SEQ ID NO 46
<211> LENGTH: 15
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal formylation
<220> FEATURE:
<221> NAME/KEY: MISC_FEATURE
<222> LOCATION: (15)..(15)
<223> OTHER INFORMATION: C-terminal amidation

<400> SEQUENCE: 46

Glu Asp Val Gln Pro Pro Gly Leu Lys Val Trp Ser Asp Pro Phe
1               5                   10                  15

<210> SEQ ID NO 47
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal formylation
<220> FEATURE:
<221> NAME/KEY: MISC_FEATURE
<222> LOCATION: (14)..(14)
<223> OTHER INFORMATION: C-terminal amidation

<400> SEQUENCE: 47

Asp Val Gln Pro Pro Gly Leu Lys Val Trp Ser Asp Pro Phe
1               5                   10

<210> SEQ ID NO 48
<211> LENGTH: 19
<212> TYPE: PRT
<213> ORGANISM: Homo sapiens
<220> FEATURE:
<221> NAME/KEY: MISC_FEATURE
<222> LOCATION: (19)..(19)
<223> OTHER INFORMATION: C-terminal modified with napthalene

<400> SEQUENCE: 48

Ala Gly Ile Val Gln Glu Asp Val Gln Pro Pro Gly Leu Lys Val Trp
1               5                   10                  15

Ser Asp Pro

<210> SEQ ID NO 49
<211> LENGTH: 13
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: C-terminal modified by napthalene

<400> SEQUENCE: 49

Asp Val Gln Pro Pro Gly Leu Lys Val Trp Ser Asp Pro
1               5                   10

<210> SEQ ID NO 50
<211> LENGTH: 12

```
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: C-terminal modified by napthalene

<400> SEQUENCE: 50

Val Gln Pro Pro Gly Leu Lys Val Trp Ser Asp Pro
1               5                   10

<210> SEQ ID NO 51
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (15)..(15)
<223> OTHER INFORMATION: C-terminal modified by napthalene

<400> SEQUENCE: 51

Xaa Glu Asp Val Gln Pro Pro Gly Leu Lys Val Trp Ser Asp Pro
1               5                   10                  15

<210> SEQ ID NO 52
<211> LENGTH: 11
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: C-terminal modified by napthalene

<400> SEQUENCE: 52

Gln Pro Pro Gly Leu Lys Val Trp Ser Asp Pro
1               5                   10

<210> SEQ ID NO 53
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid
<220> FEATURE:
<221> NAME/KEY: MISC_FEATURE
<222> LOCATION: (11)..(11)
<223> OTHER INFORMATION: C-terminal is modified by napthalene

<400> SEQUENCE: 53

Xaa Pro Pro Gly Leu Lys Val Trp Ser Asp Pro
1               5                   10

<210> SEQ ID NO 54
<211> LENGTH: 21
<212> TYPE: PRT
<213> ORGANISM: Homo sapiens

<400> SEQUENCE: 54

Ala Gly Ile Val Gln Glu Asp Val Gln Pro Pro Gly Leu Lys Val
1               5                   10                  15

Trp Ser Asp Pro Trp
            20
```

-continued

<210> SEQ ID NO 55
<211> LENGTH: 14
<212> TYPE: PRT
<213> ORGANISM: Homo sapiens

<400> SEQUENCE: 55

Asp Val Gln Pro Pro Gly Leu Lys Val Trp Ser Asp Pro Trp
1               5                   10

<210> SEQ ID NO 56
<211> LENGTH: 13
<212> TYPE: PRT
<213> ORGANISM: Homo sapiens

<400> SEQUENCE: 56

Val Gln Pro Pro Gly Leu Lys Val Trp Ser Asp Pro Trp
1               5                   10

<210> SEQ ID NO 57
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid

<400> SEQUENCE: 57

Xaa Asp Val Gln Pro Pro Gly Leu Lys Val Trp Ser Asp Pro Trp
1               5                   10                  15

<210> SEQ ID NO 58
<211> LENGTH: 12
<212> TYPE: PRT
<213> ORGANISM: Homo sapiens

<400> SEQUENCE: 58

Gln Pro Pro Gly Leu Lys Val Trp Ser Asp Pro Trp
1               5                   10

<210> SEQ ID NO 59
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X at position 1 is a pyroglutamic acid

<400> SEQUENCE: 59

Xaa Pro Pro Gly Leu Lys Val Trp Ser Asp Pro Trp
1               5                   10

<210> SEQ ID NO 60
<211> LENGTH: 15
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: tryptophan at position 11 is the D isoform

<400> SEQUENCE: 60

Asp Val Gln Pro Pro Gly Leu Lys Val Asp Trp Ser Asp Pro Trp
1               5                   10                  15

```
<210> SEQ ID NO 61
<211> LENGTH: 57
<212> TYPE: PRT
<213> ORGANISM: Homo sapiens

<400> SEQUENCE: 61

Phe Gly Gly Phe Ile Ser Leu Ile Gly Ala Ala Phe Tyr Pro Ile Tyr
 1               5                   10                  15

Phe Arg Pro Leu Met Arg Leu Glu Glu Tyr Lys Lys Glu Gln Ala Ile
                20                  25                  30

Asn Arg Ala Gly Ile Val Gln Glu Asp Val Gln Pro Pro Gly Leu Lys
            35                  40                  45

Val Trp Ser Asp Pro Phe Gly Arg Lys
        50                  55

<210> SEQ ID NO 62
<211> LENGTH: 57
<212> TYPE: PRT
<213> ORGANISM: Mus

<400> SEQUENCE: 62

Phe Gly Gly Phe Ile Ser Met Val Gly Ala Ala Phe Tyr Pro Ile Tyr
 1               5                   10                  15

Phe Arg Pro Leu Leu Arg Leu Glu Glu Tyr Gln Lys Glu Gln Ala Val
                20                  25                  30

Asn Arg Ala Gly Ile Val Gln Glu Asp Val Gln Pro Pro Gly Leu Lys
            35                  40                  45

Val Trp Ser Asp Pro Phe Gly Arg Lys
        50                  55

<210> SEQ ID NO 63
<211> LENGTH: 57
<212> TYPE: PRT
<213> ORGANISM: Rattus

<400> SEQUENCE: 63

Phe Gly Gly Phe Ile Ser Met Val Gly Ala Ala Phe Tyr Pro Ile Tyr
 1               5                   10                  15

Phe Arg Pro Leu Leu Arg Leu Glu Glu Tyr Gln Lys Glu Gln Ala Val
                20                  25                  30

Asn Arg Ala Gly Ile Val Gln Glu Asp Val Gln Pro Pro Gly Leu Lys
            35                  40                  45

Val Trp Ser Asp Pro Phe Gly Arg Lys
        50                  55

<210> SEQ ID NO 64
<211> LENGTH: 57
<212> TYPE: PRT
<213> ORGANISM: Sus scrofa

<400> SEQUENCE: 64

Phe Gly Gly Phe Ile Ser Leu Ile Gly Ala Ala Phe Tyr Pro Ile Tyr
 1               5                   10                  15

Phe Arg Pro Leu Met Arg Leu Glu Glu Tyr Gln Lys Glu Gln Ala Ile
                20                  25                  30

Asn Arg Ala Gly Val Val Gln Glu Asp Val Gln Pro Pro Gly Leu Lys
            35                  40                  45

Val Trp Ser Asp Pro Phe Gly Arg Lys
        50                  55
```

```
<210> SEQ ID NO 65
<211> LENGTH: 57
<212> TYPE: PRT
<213> ORGANISM: Bos taurus

<400> SEQUENCE: 65

Phe Gly Gly Phe Ile Ser Leu Ile Gly Ala Ala Phe Tyr Pro Ile Tyr
1               5                   10                  15

Phe Arg Pro Leu Met Arg Leu Glu Glu Tyr Lys Lys Glu Gln Ala Ile
            20                  25                  30

Asn Arg Ala Gly Ile Val Gln Glu Asp Val Gln Pro Gly Leu Lys
        35                  40                  45

Val Trp Ser Asp Pro Phe Gly Arg Lys
    50                  55

<210> SEQ ID NO 66
<211> LENGTH: 47
<212> TYPE: PRT
<213> ORGANISM: Canis

<400> SEQUENCE: 66

Ala Phe Tyr Pro Ile Tyr Phe Arg Pro Leu Leu Leu Pro Glu Glu Tyr
1               5                   10                  15

Gln Lys Glu Gln Ala Val Asn Arg Ala Gly Ile Ile Gln Glu Asp Val
            20                  25                  30

Gln Pro Pro Gly Leu Lys Val Trp Ser Asp Pro Phe Gly Arg Lys
        35                  40                  45
```